US012721851B2

(12) United States Patent
Tamai et al.

(10) Patent No.: US 12,721,851 B2
(45) Date of Patent: Sep. 1, 2026

(54) PHARMACEUTICAL COMPOSITION FOR TREATING SOLID TUMORS

(71) Applicant: Eisai R&D Management Co., Ltd., Tokyo (JP)

(72) Inventors: Toshiyuki Tamai, Tokyo (JP); Satoshi Nagao, Tokyo (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 234 days.

(21) Appl. No.: 18/293,848

(22) PCT Filed: Sep. 6, 2022

(86) PCT No.: PCT/JP2022/033458
§ 371 (c)(1),
(2) Date: Jan. 31, 2024

(87) PCT Pub. No.: WO2023/038030
PCT Pub. Date: Mar. 16, 2023

(65) Prior Publication Data

US 2025/0222003 A1 Jul. 10, 2025

(30) Foreign Application Priority Data

Sep. 8, 2021 (JP) ................................ 2021-146389

(51) Int. Cl.

| | |
|---|---|
| ***A61K 31/53*** | (2006.01) |
| ***A61K 31/4184*** | (2006.01) |
| ***A61K 31/439*** | (2006.01) |
| ***A61P 1/08*** | (2006.01) |
| ***A61P 35/00*** | (2006.01) |

(52) U.S. Cl.
CPC .......... *A61K 31/53* (2013.01); *A61K 31/4184* (2013.01); *A61K 31/439* (2013.01); *A61P 1/08* (2018.01); *A61P 35/00* (2018.01)

(58) Field of Classification Search
CPC .. A61K 31/53; A61K 31/4184; A61K 31/439; A61P 1/08; A61P 35/00
See application file for complete search history.

(56) References Cited

U.S. PATENT DOCUMENTS

| | | | |
|---|---|---|---|
| 6,262,046 | B1 | 7/2001 | Alker et al. |
| 7,101,872 | B2 | 9/2006 | Bachmann et al. |
| RE39,682 | E | 6/2007 | Kloog |
| 7,378,423 | B2 | 5/2008 | Kawasaki et al. |
| 7,777,050 | B2 | 8/2010 | Wallace et al. |
| 7,803,839 | B2 | 9/2010 | Aay et al. |
| 8,080,657 | B2 | 12/2011 | Chung et al. |
| 8,143,271 | B2 | 3/2012 | Ibrahim et al. |
| 8,415,345 | B2 | 4/2013 | Adjabeng et al. |
| 8,501,758 | B2 | 8/2013 | Huang et al. |
| 8,741,920 | B2 | 6/2014 | Hildbrand et al. |
| 9,174,988 | B2 | 11/2015 | Snyder et al. |
| 9,174,998 | B2 | 11/2015 | Inoue et al. |
| 9,861,623 | B1 | 1/2018 | Liu et al. |
| 10,259,817 | B2 | 4/2019 | Kushida et al. |
| 10,370,386 | B2 | 8/2019 | Li et al. |
| 10,519,146 | B2 | 12/2019 | Lanman et al. |

(Continued)

FOREIGN PATENT DOCUMENTS

| | | |
|---|---|---|
| CA | 3044658 A1 | 8/2018 |
| CL | 201102116 | 3/2009 |

(Continued)

OTHER PUBLICATIONS

Submission Document in European Patent Application No. 22867352.1, dated May 17, 2024, 8 pages.
Submission Document in Taiwanese Patent Application No. 111133779, dated Dec. 26, 2025, 86 pages (with English translation).
Submission Document in Russian Patent Application No. 2024102374, dated Sep. 8, 2025, 4 pages.
International Search Report in International Application No. PCT/JP2022/033458, mailed on Nov. 22, 2022, 2 pages (English Translation).

(Continued)

*Primary Examiner* — Jeffrey S Lundgren
*Assistant Examiner* — W. Justin Youngblood
(74) *Attorney, Agent, or Firm* — Fish & Richardson P.C.

(57) ABSTRACT

The present invention provides a pharmaceutical composition for treating a solid tumor, comprising (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4] triazine-1(6H)-carboxamide (Compound A) represented by the formula (I) or a pharmaceutically acceptable salt thereof, wherein the pharmaceutical composition is administered to a human subject together with an effective amount of a 5-$HT_3$ receptor antagonist to suppress gastrointestinal symptoms in such a manner that Compound A or the pharmaceutically acceptable salt thereof is administered twice daily at a dose of about 10 mg to about 150 mg per dose of Compound A; and the gastrointestinal symptom is a gastrointestinal symptom associated with administration of Compound A or a pharmaceutically acceptable salt thereof

[Chemical Formula 1]

(I)

20 Claims, 5 Drawing Sheets

(56) References Cited

U.S. PATENT DOCUMENTS

| | | | | |
|---|---|---|---|---|
| 10,689,377 | B2 | 6/2020 | Blake et al. | |
| 10,898,487 | B2 | 1/2021 | Kessler et al. | |
| 11,091,481 | B2 | 8/2021 | Dai | |
| 11,236,068 | B2 | 2/2022 | Malhotra et al. | |
| 2004/0147510 | A1 | 7/2004 | Landau et al. | |
| 2007/0043052 | A1 | 2/2007 | Moon et al. | |
| 2009/0069421 | A1 | 3/2009 | Kasai et al. | |
| 2010/0286094 | A1 | 11/2010 | Chung et al. | |
| 2011/0092459 | A1 | 4/2011 | Odagami et al. | |
| 2011/0288115 | A1 | 11/2011 | Kelbe | |
| 2013/0196972 | A1 | 8/2013 | Chung et al. | |
| 2015/0005343 | A1 | 1/2015 | Nomoto et al. | |
| 2015/0175615 | A1 * | 6/2015 | Inoue | A61P 35/00 544/184 |
| 2016/0045502 | A1 | 2/2016 | Brown | |
| 2018/0038868 | A1 | 2/2018 | Gajewski et al. | |
| 2018/0141950 | A1 | 5/2018 | Kushida et al. | |
| 2019/0388420 | A1 | 12/2019 | Ozawa et al. | |
| 2020/0163939 | A1 | 5/2020 | Garner et al. | |
| 2020/0297711 | A1 | 9/2020 | Sasaki et al. | |

FOREIGN PATENT DOCUMENTS

| | | | |
|---|---|---|---|
| CL | 200003576 | | 10/2009 |
| CL | 201402511 | | 4/2012 |
| CL | 201502363 | | 2/2013 |
| CL | 201601367 | | 2/2013 |
| CN | 1585770 | A | 2/2005 |
| CN | 101827849 | A | 9/2010 |
| CN | 101896485 | A | 11/2010 |
| CN | 102046628 | A | 5/2011 |
| CN | 103209982 | A | 7/2013 |
| CN | 105338977 | A | 2/2016 |
| CN | 111050768 | A | 4/2020 |
| EP | 2206517 | A1 | 7/2010 |
| EP | 2628741 | A2 | 8/2013 |
| EP | 3088401 | A1 | 11/2016 |
| JP | 2011-500666 | A | 1/2011 |
| JP | 2011-522037 | A | 7/2011 |
| JP | 2013-540774 | A | 11/2013 |
| JP | 2014-509298 | A | 4/2014 |
| JP | 2016-528162 | A | 9/2016 |
| RU | 2457210 | C2 | 7/2012 |
| RU | 2470024 | C2 | 12/2012 |
| RU | 2512538 | C2 | 4/2014 |
| RU | 2669805 | C2 | 10/2018 |
| WO | WO 2001/046196 | A1 | 6/2001 |
| WO | WO 2003/077914 | A1 | 9/2003 |
| WO | WO 2006/123517 | A1 | 11/2006 |
| WO | WO 2009/051397 | A2 | 4/2009 |
| WO | WO 2009/148192 | A1 | 12/2009 |
| WO | WO 2010/101849 | A1 | 9/2010 |
| WO | WO 2010/120112 | A2 | 10/2010 |
| WO | WO 2012/115286 | A1 | 8/2012 |
| WO | WO 2012/154935 | A1 | 11/2012 |
| WO | WO 2013/151708 | A1 | 10/2013 |
| WO | WO 2014/061826 | A1 | 4/2014 |
| WO | WO 2014/128245 | A1 | 8/2014 |
| WO | WO 2014/130869 | A1 | 8/2014 |
| WO | WO 2014/208774 | A1 | 12/2014 |
| WO | WO 2015/098853 | | 7/2015 |
| WO | WO 2015/098855 | A1 | 7/2015 |
| WO | WO 2016/141218 | A1 | 9/2016 |
| WO | WO 2016/204193 | A1 | 12/2016 |
| WO | WO 2016/208576 | | 12/2016 |
| WO | WO 2018/147275 | | 8/2018 |
| WO | WO 2020/173935 | A1 | 9/2020 |
| WO | WO 2021/041671 | A1 | 3/2021 |
| WO | WO 2021/086909 | | 5/2021 |
| WO | WO 2021/124222 | A1 | 6/2021 |
| WO | WO 2022/031952 | A2 | 2/2022 |

OTHER PUBLICATIONS

Kawazoe et al., "A phase I study of E7386,a CREB-binding protein(CBP)/β-catenin interaction inhibitor, in patients with advanced solid tumors including colorectal cancer(CRC)," Abstract, Annals of Oncology, Sep. 21, 2021, 32(S5):S567.

Office Action in Japanese Patent Application No. P2023-546948, Nov. 7, 2023, 6 pages (with English Translation).

Chandler et al., "β-Catenin/CBP inhibition alters epidermal growth factor receptor fucosylation status in oral squamous cell carcinoma," Molecular Omics, Jan. 2020, 16(3):195-209.

Notice of Allowance in U.S. Appl. No. 16/465,277, dated Apr. 9, 2025, 6 pages.

Notice of Allowance in U.S. Appl. No. 16/465,277, dated Mar. 31, 2025, 7 pages.

Office Action in European Patent Application No. 18751614.1, dated Feb. 20, 2025, 12 pages.

Opposition, "Lenvima," Exhibit D9 in European Application No. 18751614.1, dated May 20, 2020, 61 pages.

Search Report in European Patent Application No. 22867352.1, dated May 28, 2025, 9 pages.

Submission Document in European Patent Application No. 22867352.1, dated Sep. 18, 2025, 66 pages.

International Preliminary Report on Patentability in International Application No. PCT/JP2022/033458, dated Mar. 21, 2024, 5 pages.

Notice of Allowance in Thai Patent Application No. 1601003377, dated Jan. 30, 2025, 2 pages (with English Translation).

Notice of Allowance in U.S. Appl. No. 16/465,277, dated Feb. 3, 2025, 11 pages.

Notice of Allowance in U.S. Appl. No. 16/465,277, dated Nov. 15, 2024, 12 pages.

Submission Document in European Patent Application No. 23780756.5, dated Feb. 6, 2025, 6 pages.

Submission Document in U.S. Appl. No. 16/465,277, dated Jan. 16, 2025, 12 pages.

Submission Document in Taiwanese Patent Application No. 111133779, dated May 23, 2025, 13 pages (with English Translation).

Office Action in European Patent Application No. 22867352.1, dated Jun. 17, 2025, 1 page.

Notice of Allowance in Taiwanese Patent Application No. 111133779, dated Jan. 21, 2026, 4 pages (with English translation).

[No Author], "Original Specification of Opposed Application," EISAI R&D Management Co., Ltd, Jun. 7, 2019, 40 pages.

Azuma, "Cancer Immunotherapy by Blockade of PD-1 Immune Checkpoint," Journal of Clinical and Experimental Medicine, Mar. 2, 2013, 244(9):809-815 (with Full Translation).

Barker and Clevers, "Mining the Wnt pathway for cancer therapeutics," Reviews Drug Discovery, Dec. 2006, 5:997-1014.

Bennett et al., "Cecil Textbook of Medicine," W.B. Saunders Company, 1996, 20th ed., vol. 1, pp. 1004-1010.

Chen et al., "Solid-state nuclear magnetic resonance and its application in research of drug polymorphs," Chinese Journal of New Drugs, 2013, 22(16):1921-1924, 1955 (with English Translation).

Chen et al., "Small molecule-mediated disruption of Wnt-dependent signaling in tissue regeneration and cancer," Nat Chem Biol., Feb. 2009, 5(2):100-107.

De Robertis et al., "Identification and characterization of a small-molecule inhibitor of Wnt signaling in glioblastoma cells," Mol Cancer Ther, 2013, 12:1180-1189.

Dermer, "Another Anniversary for the War on Cancer," Bio/Technology, 1994 12:320, 8 pages.

Emami et al., "A small molecule inhibitor of β-catenin /CREB-binding protein transcription," PNAS, Aug. 24, 2004, 101(34):12682-12687.

Fodde et al., "Wnt/β-catenin signaling in cancer stemness and malignant behavior," Current Opinion in Cell Biology, 2007, 19(2):150-158.

Freshney, "Culture of Animal Cells," A Manual of Basic Technique, Alan R. Liss, Inc., 1983, pp. 1-6.

Gurney et al., "Wnt pathway inhibition via the targeting of Frizzled receptors results in decreased growth and tumorigenicity of human tumors," PNAS, Jul. 17, 2012, 109(29):11717-11722.

(56) References Cited

OTHER PUBLICATIONS

Hao et al., "Targeted Inhibition of β-Catenin/CBP Signaling Ameliorates Renal Interstitial Fibrosis," J Am Soc Nephrol., Sep. 2011, 22(9):1642-1653.
Henderson Jr et al., "Inhibition of Wnt/β-catenin/CREB binding protein(CBP) signaling reverses pulmonary fibrosis," PNAS, Aug. 10, 2010, 107(32):14309-14314.
Huang et al., "Tankyrase inhibition stabilizes axin and antagonizes Wnt signaling," Nature, 2009, 461(7264):614-620.
International Preliminary Report on Patentability in International Patent Application No. PCT/JP2014/083932, dated Jul. 7, 2016, 5 pages.
International Preliminary Report on Patentability in International Patent Application No. PCT/JP2016/068381, dated Jan. 4, 2018, 9 pages (English Translation).
International Preliminary Report on Patentability in International Patent Application No. PCT/JP2018/004007, dated Aug. 22, 2019, 7 pages.
International Preliminary Report on Patentability in International Patent Application No. PCT/JP2023/012957, dated Oct. 10, 2024, 5 pages.
International Search Report and Written Opinion in International Patent Application No. PCT/JP2014/083932, dated Mar. 17, 2015, 14 pages (with English Translation).
International Search Report and Written Opinion in International Patent Application No. PCT/US2020/057650, dated Feb. 12, 2021, 16 pages.
International Search Report in International Patent Application No. PCT/JP2016/068381, mailed on Sep. 6, 2016, 2 pages (English Translation).
International Search Report in International Patent Application No. PCT/JP2023/012957, dated Jun. 20, 2023, 2 pages (English Translation).
Jeong et al., "Interaction between Wnt/β-catenin and RAS-ERK pathways and an anti-cancer strategy via degradations of β-catenin and RAS by targeting the Wnt/β-catenin pathway," NPJ Precision Onc., Feb. 20, 2018, 2(5):1-10.
Jiang et al., "Inactivating mutations of RNF43 confer Wnt dependency in pancreatic ductal adenocarcinoma," PNAS, Jul. 30, 2013, 110(31):12649-12654.
Kim et al., "Combining targeted therapy and immune checkpoint inhibitors in the treatment of metastatic melanoma," Cancer Biol. Med., Dec. 2014, 11(4):237-246.
Lam et al., "β-catenin signaling: a novel mediator of fibrosis and potential therapeutic target," Curr Opin Rheumatol., 2011, 23(6):562-567 (Author Manuscript).
Lehtio et al., "Tankyrases as drug targets," FEBS J., 2013, 280:3576-3593.
Lenz et al., "Safely targeting cancer stem cells via selective catenin coactivator antagonism," Cancer Sci., Sep. 2014, 105(9):1087-1092.
Mahoney et al., "The Next Immune-Checkpoint Inhibitors: PD-1/PD-L1 Blockade in Melanoma," Clin. Ther., Apr. 2015, 37(4):764-782.
Molina et al., "A phase 1b clinical trial of the multitargeted tyrosine kinase inhibitor lenvatinib (E7080) in combination with everolimus for treatment of metastatic renal cell carcinoma (RCC)," Cancer Chemotherapy and Pharmacology, Jan. 2014, 73(1):181-189.
Mologni et al., "Synergistic Effects of Combined Wnt/KRAS Inhibition in Colorectal Cancer Cells," PLoS One, Dec. 5, 2012, 7(12):1-10.
Notice of Allowance in Argentina Patent Application No. P140104850, dated Mar. 26, 2024, 4 pages (with English Translation).
Notice of Allowance in Australian Patent Application No. 2014371148, dated Jul. 26, 2018, 4 pages (English Translation).
Notice of Allowance in Australian Patent Application No. 2016284383, dated Aug. 10, 2020, 47 pages.
Notice of Allowance in Brazilian Patent Application No. BR112016013572-5, dated Mar. 7, 2023, 295 pages (with English Translation).
Notice of Allowance in Brazilian Patent Application No. BR112016013572-5, dated Nov. 8, 2022, 10 pages (with English Translation).
Notice of Allowance in Brazilian Patent Application No. BR112017025519-7, dated Jun. 6, 2023, 7 pages (with English Translation).
Notice of Allowance in Canadian Patent Application No. 2932435, dated Apr. 27, 2021, 2 pages.
Notice of Allowance in Canadian Patent Application No. 2986999, dated Mar. 28, 2023, 1 page.
Notice of Allowance in Chinese Patent Application No. 201480067017.7, dated Sep. 13, 2018, 4 pages (English Translation).
Notice of Allowance in Chinese Patent Application No. 201680030060.5, Nov. 4, 2019, 4 pages (with English Translation).
Notice of Allowance in Chinese Patent Application No. 201880005026.1, dated Feb. 25, 2022, 8 pages (with English Translation).
Notice of Allowance in European Patent Application No. 14873998.0, dated Oct. 17, 2018, 141 pages.
Notice of Allowance in European Patent Application No. 16814346.9, dated Nov. 25, 2020, 37 pages.
Notice of Allowance in European Patent Application No. 18751614.1, dated Jun. 26, 2023, 66 pages.
Notice of Allowance in Gulf Cooperation Council Patent Application No. GC2014-28624, dated May 9, 2018, 2 pages (English Translation).
Notice of Allowance in Indonesian Patent Application No. P00201603922, dated Jul. 15, 2019, 4 pages (with English Translation).
Notice of Allowance in Israeli Patent Application No. 245961, dated Jul. 26, 2018, 15 pages (English Translation).
Notice of Allowance in Israeli Patent Application No. 255901, dated Apr. 27, 2020, 5 pages (with English Translation).
Notice of Allowance in Israeli Patent Application No. 267159, dated Mar. 2, 2022, 6 pages (with English Translation).
Notice of Allowance in Japanese Patent Application No. P2015-554886, dated Jan. 24, 2017, 6 pages, (English Translation).
Notice of Allowance in Japanese Patent Application No. P2016-572771, dated Apr. 4, 2017, 6 pages (English Translation).
Notice of Allowance in Japanese Patent Application No. P2018-567437, dated Aug. 27, 2019, 5 pages (with English Translation).
Notice of Allowance in Korean Patent Application No. 10-2016-7015608, dated Jun. 29, 2021, 4 pages (with English Translation).
Notice of Allowance in Korean Patent Application No. 10-2017-7033876, dated Jun. 23, 2023, 7 pages (with English Translation).
Notice of Allowance in Korean Patent Application No. 10-2019-7016853, dated Mar. 24, 2023, 7 pages (with English Translation).
Notice of Allowance in Malaysian Patent Application No. PI2016702025, dated Feb. 12, 2020, 3 pages.
Notice of Allowance in Mexican Patent Application No. MX/a/2016/007705, dated Apr. 5, 2019, 5 pages (with English Translation).
Notice of Allowance in Mexican Patent Application No. MX/a/2017/015257, dated Apr. 22, 2021, 4 pages (with English Translation).
Notice of Allowance in Mexican Patent Application No. MX/a/2019/006504, dated Jan. 13, 2021, 6 pages (with English Translation).
Notice of Allowance in New Zealand Patent Application No. 720718, dated Oct. 7, 2020, 2 pages.
Notice of Allowance in Pakistani Patent Application No. 907/2014, dated May 2, 2018, 1 page (English Translation).
Notice of Allowance in Russian Patent Application No. 2016122867, dated Aug. 31, 2018, 30 pages (English Translation).
Notice of Allowance in Russian Patent Application No. 2017141763, dated Apr. 28, 2020, 13 pages (with English Translation).
Notice of Allowance in Singaporean Patent Application No. 11201604496Y, dated Nov. 23, 2016, 5 pages.
Notice of Allowance in Singaporean Patent Application No. 11201709593V, dated Jan. 27, 2023, 4 pages.
Notice of Allowance in Singaporean Patent Application No. 11201904020S, dated Sep. 30, 2021, 4 pages.
Notice of Allowance in South African Patent Application No. 2016/03956, dated Nov. 2, 2017, 2 pages.

(56) References Cited

OTHER PUBLICATIONS

Notice of Allowance in Taiwanese Patent Application No. 103144928, dated Oct. 31, 2019, 6 pages (with English Translation).
Notice of Allowance in U.S. Appl. No. 14/577,660, dated Jul. 9, 2015, 10 pages.
Notice of Allowance in U.S. Appl. No. 16/465,277, dated Apr. 26, 2021, 12 pages.
Notice of Allowance in U.S. Appl. No. 16/465,277, dated Apr. 4, 2023, 6 pages.
Notice of Allowance in U.S. Appl. No. 16/465,277, dated Aug. 1, 2022, 37 pages.
Notice of Allowance in U.S. Appl. No. 16/465,277, dated Dec. 6, 2023, 6 pages.
Notice of Allowance in U.S. Appl. No. 16/465,277, dated Dec. 7, 2022, 13 pages.
Notice of Allowance in U.S. Appl. No. 16/465,277, dated Jan. 12, 2022, 11 pages.
Notice of Allowance in U.S. Appl. No. 16/465,277, dated Jan. 30, 2024, 6 pages.
Notice of Allowance in U.S. Appl. No. 16/465,277, dated Jul. 20, 2023, 15 pages.
Notice of Allowance in U.S. Appl. No. 16/465,277, dated Jul. 9, 2024, 12 pages.
Notice of Allowance in U.S. Appl. No. 16/465,277, dated Jun. 25, 2020, 16 pages.
Notice of Allowance in U.S. Appl. No. 16/465,277, dated Mar. 26, 2024, 11 pages.
Notice of Allowance in U.S. Appl. No. 16/465,277, dated Mar. 9, 2023, 13 pages.
Notice of Allowance in U.S. Appl. No. 16/465,277, dated Nov. 2, 2023, 12 pages.
Notice of Allowance in U.S. Appl. No. 16/465,277, dated Nov. 21, 2022, 11 pages.
Notice of Allowance in U.S. Appl. No. 16/465,277, dated Oct. 17, 2024, 13 pages.
Notice of Allowance in U.S. Appl. No. 16/465,277, dated Oct. 21, 2020, 11 pages.
Notice of Allowance in U.S. Appl. No. 16/465,277, dated Sep. 16, 2021, 43 pages.
Notice of Allowance in U.S. Appl. No. 16/465,277, dated Sep. 18, 2023, 6 pages.
Notice of Allowance in Ukraine Patent Application No. a201606261, dated Feb. 22, 2018, 18 pages (English Translation).
Notice of Allowance in Venezuelan Patent Application No. 2014001560, dated Jul. 22, 2022, 3 pages (with English Translation).
Notice of Allowance in Vietnamese Patent Application No. 1-2016-02104, dated Aug. 27, 2018, 2 pages (English Translation).
Office Action in Argentina Patent Application No. P140104850, dated Dec. 18, 2019, 4 pages (with English Translation).
Office Action in Argentina Patent Application No. P140104850, dated Sep. 13, 2023, 10 pages (with English Translation).
Office Action in Australian Patent Application No. 2014371148, dated Mar. 28, 2018, 2 pages.
Office Action in Australian Patent Application No. 2016284383, dated Jun. 3, 2020, 3 pages.
Office Action in Australian Patent Application No. 2016284383, dated Mar. 23, 2020, 3 pages.
Office Action in Australian Patent Application No. 2018219637, dated Jun. 30, 2023, 3 pages.
Office Action in Australian Patent Application No. 2018219637, dated Mar. 14, 2023, 9 pages.
Office Action in Brazilian Patent Application No. BR112016013572-5, dated Feb. 11, 2020, 9 pages (with English Translation).
Office Action in Brazilian Patent Application No. BR112017025519-7, dated Feb. 14, 2023, 9 pages (with English Translation).
Office Action in Brazilian Patent Application No. BR112017025519-7, dated Nov. 24, 2020, 9 pages (with English Translation).
Office Action in Brazilian Patent Application No. BR1120190141278, dated Jul. 26, 2022, 8 pages (with English Translation).
Office Action in Canadian Patent Application No. 2932435, dated Oct. 9, 2020, 3 pages.
Office Action in Canadian Patent Application No. 2986999, dated Mar. 25, 2022, 4 pages.
Office Action in Canadian Patent Application No. 2986999, dated Sep. 9, 2022, 3 pages.
Office Action in Canadian Patent Application No. 3044658, dated Feb. 20, 2024, 4 pages.
Office Action in Chilean Patent Application No. 201601419, dated Feb. 13, 2018, 18 pages (English Translation).
Office Action in Chinese Patent Application No. 201480067017.7, dated Mar. 1, 2017, 11 pages (English Translation).
Office Action in Chinese Patent Application No. 201680030060.5, dated Jan. 30, 2019, 15 pages (with English Translation).
Office Action in Chinese Patent Application No. 201680030060.5, dated Jul. 15, 2019, 8 pages (with English Translation).
Office Action in Chinese Patent Application No. 201880005026.1, dated Dec. 21, 2021, 6 pages (with English Translation).
Office Action in Chinese Patent Application No. 201880005026.1, dated Dec. 9, 2021, 17 pages (with English Translation).
Office Action in Chinese Patent Application No. 201880005026.1, dated Jul. 29, 2021, 10 pages (with English Translation).
Office Action in Colombian Patent Application No. 16147681, dated Jun. 27, 2018, 16 pages (English Translation).
Office Action in Egyptian Patent Application No. PCT985-2016, dated Jan. 10, 2024, 11 pages (with English Translation).
Office Action in Egyptian Patent Application No. PCT985-2016, dated Jan. 15, 2023, 9 pages (with English Translation).
Office Action in Egyptian Patent Application No. PCT985-2016, dated Jan. 2, 2022, 9 pages (with English Translation).
Office Action in European in Patent Application No. 16814346.9, dated Feb. 27, 2020, 3 pages.
Office Action in European Patent Application No. 16814346.9, dated Jun. 26, 2019, 5 pages.
Office Action in Gulf Cooperation Council Patent Application No. GC2014-28624, dated Jan. 7, 2018, 7 pages (English Translation).
Office Action in Indian Patent Application No. 201647019978, dated Apr. 29, 2019, 6 pages.
Office Action in Indian Patent Application No. 201647019978, Sep. 16, 2019, 2 pages.
Office Action in Indian Patent Application No. 201747042429, dated Jan. 28, 2020, 6 pages.
Office Action in Indian Patent Application No. 201747042429, dated Oct. 20, 2022, 2 pages.
Office Action in Indian Patent Application No. 201947022655, dated Feb. 13, 2024, 335 pages.
Office Action in Indian Patent Application No. 201947022655, dated Jan. 19, 2021, 5 pages (with English Translation).
Office Action in Indian Patent Application No. 201947022655, dated Oct. 25, 2021, 2 pages (with English Translation).
Office Action in Indian Patent Application No. 202148057534, dated Feb. 4, 2022, 5 pages (with English Translation).
Office Action in Indian Patent Application No. 202148057534, dated Mar. 14, 2023, 2 pages (with English Translation).
Office Action in Indian Patent Application No. 202148057534, dated May 1, 2023, 2 pages.
Office Action in Indonesian Patent Application No. P00201603922, dated Feb. 21, 2019, 6 pages (with English Translation).
Office Action in Israeli Patent Application No. 245961, dated Jul. 20, 2016, 5 pages (English Translation).
Office Action in Israeli Patent Application No. 255901, dated Nov. 8, 2018, 5 pages (with English Translation).
Office Action in Israeli Patent Application No. 267159, dated Feb. 5, 2020, 5 pages (with English Translation).
Office Action in Israeli Patent Application No. 267159, dated Oct. 6, 2021, 8 pages (with English Translation).
Office Action in Japanese Patent Application No. P2016-572771, dated Feb. 7, 2017, 6 pages (English Translation).
Office Action in Jordanian Patent Application No. 3732014, dated Jan. 6, 2020, 2 pages (with English Translation).
Office Action in Korean Application No. 10-2016-7015608, dated Jan. 18, 2021, 5 pages (with English Translation).

(56) References Cited

OTHER PUBLICATIONS

Office Action in Korean Patent Application No. 10-2017-7033876, dated Feb. 3, 2023, 9 pages (with English Translation).
Office Action in Korean Patent Application No. 10-2019-7016853, dated Jan. 8, 2023, 7 pages (with English Translation).
Office Action in Mexican Patent Application No. MX/a/2017/015257, dated Feb. 2, 2021, 6 pages (with English Translation).
Office Action in Mexican Patent Application No. MX/a/2017/015257, dated Oct. 2, 2020, 9 pages (with English Translation).
Office Action in Mexican Patent Application No. MX/a/2019/006504, dated Sep. 3, 2020, 10 pages (with English Translation).
Office Action in New Zealand Patent Application No. 720718, dated Aug. 14, 2020, 2 pages.
Office Action in Pakistani Patent Application No. 907/2014, dated Aug. 11, 2016, 2 pages.
Office Action in Peruvian Patent Application No. 000711-2016, dated Oct. 11, 2019, 14 pages (with English Translation).
Office Action in Russian Patent Application No. 2016122867, dated Jun. 18, 2018, 13 pages (English Translation).
Office Action in Russian Patent Application No. 2017141763, dated Aug. 23, 2019, 16 pages (with English Translation).
Office Action in Russian Patent Application No. 2017141763, dated Jan. 10, 2020, 11 pages (with English Translation).
Office Action in Russian Patent Application No. 2019120680, dated Dec. 28, 2020, 18 pages (with English Translation).
Office Action in Russian Patent Application No. 2019120680, dated May 12, 2021, 13 pages (with English Translation).
Office Action in Singaporean Patent Application No. 11201709593V, dated Dec. 24, 2020, 6 pages.
Office Action in Singaporean Patent Application No. 11201904020S, dated May 19, 2021, 5 pages.
Office Action in Taiwanese Patent Application No. 103144928, dated Jun. 7, 2018, 7 pages (English Translation).
Office Action in Taiwanese Patent Application No. 103144928, dated Nov. 13, 2018, 6 pages (English Translation).
Office Action in U.S. Appl. No. 16/465,277, dated Mar. 20, 2020, 150 pages.
Office Action in Vietnamese Patent Application No. 1-2016-02104, dated Apr. 26, 2018, 4 pages (English Translation).
Official Notification in Chilean Patent Application No. 201601419, dated Sep. 21, 2018, 17 pages (English Translation).
Official Notification in Gulf Cooperation Council Patent Application No. GC2014-28624, dated Apr. 5, 2018, 298 pages (English Translation).
Santos et al., "Structural and functional properties of ras proteins," FASEB J., Aug. 1989, 3(10):2151-2163.
Search Report in European Patent Application No. 14873998.0, dated May 29, 2017, 6 pages.
Search Report in European Patent Application No. 16814346.9, dated Nov. 15, 2018, 8 pages.
Search Report in European Patent Application No. 18751614.1, dated Nov. 5, 2020, 8 pages.
Shah et al., "CTLA-4 is a direct target of Wnt/β-catenin signaling and is expressed in human melanoma tumors," Journal of Investigative Dermatology, 2008, 128(12):2870-2879.
Shitashige et al., "Traf2- and Nck-Interacting Kinase Is Essential for Wnt Signaling and Colorectal Cancer Growth," Cancer Res., 2010, 70:5024-5033.
Spranger et al., "Melanoma-intrinsic β-catenin signalling prevents anti-tumour immunity," Nature, Jul. 9, 2015, 523(7559):231-235.
Submission Document in Argentina Patent Application No. P140104850, dated Feb. 6, 2020, 183 pages (with English Translation).
Submission Document in Argentina Patent Application No. P140104850, dated Feb. 6, 2024, 5 pages (with English Translation).
Submission Document in Australian Patent Application No. 2014371148, date Jul. 10, 2018, 8 pages.
Submission Document in Australian Patent Application No. 2016284383, dated Jul. 31, 2020, 7 pages.
Submission Document in Australian Patent Application No. 2016284383, dated May 12, 2020, 26 pages.
Submission Document in Australian Patent Application No. 2018219637, dated Jun. 7, 2023, 17 pages.
Submission Document in Brazilian Patent Application No. BR112016013572-5, dated May 11, 2020, 22 pages (with English Translation).
Submission Document in Brazilian Patent Application No. BR112017025519-7, dated Feb. 18, 2021, 12 pages (with English Translation).
Submission Document in Brazilian Patent Application No. BR112017025519-7, dated May 12, 2023, 20 pages (with English Translation).
Submission Document in Brazilian Patent Application No. BR1120190141278, dated Dec. 16, 2020, 16 pages (with English Translation).
Submission Document in Brazilian Patent Application No. BR1120190141278, dated Oct. 19, 2022, 4 pages (with English Translation).
Submission Document in Canadian Patent Application No. 2932435, dated Jan. 26, 2021, 15 pages.
Submission Document in Canadian Patent Application No. 2986999, dated Jun. 6, 2022, 25 pages.
Submission Document in Canadian Patent Application No. 2986999, dated Nov. 11, 2022, 6 pages.
Submission Document in Chilean Patent Application No. 201601419, dated Jul. 13, 2018, 30 pages (English Translation).
Submission Document in Chinese Patent Application No. 201480067017.7, dated Jun. 5, 2017, 7 pages, (English Translation).
Submission Document in Chinese Patent Application No. 201680030060.5, dated Aug. 21, 2019, 61 pages (with English Translation).
Submission Document in Chinese Patent Application No. 201880005026.1, dated Feb. 14, 2022, 17 pages (with English Translation).
Submission Document in Colombian Patent Application No. 16147681, date Oct. 30, 2017, 39 pages (English Translation).
Submission Document in Egyptian Patent Application No. PCT985-2016, dated Apr. 4, 2022, 7 pages (with English Translation).
Submission Document in Egyptian Patent Application No. PCT985-2016, dated Apr. 6, 2023, 11 pages (with English Translation).
Submission Document in European Patent Application No. 14873998.0, dated Dec. 13, 2017, 11 pages.
Submission Document in European Patent Application No. 16814346.9, dated Feb. 22, 2019, 9 pages.
Submission Document in European Patent Application No. 16814346.9, dated Jun. 18, 2020, 9 pages.
Submission Document in European Patent Application No. 16814346.9, dated Sep. 23, 2019, 45 pages.
Submission Document in European Patent Application No. 18751614.1, dated Dec. 18, 2020, 6 pages.
Submission Document in Indian Patent Application No. 201647019978, dated Jul. 30, 2019, 28 pages.
Submission Document in Indian Patent Application No. 201647019978, dated Oct. 31, 2019, 11 pages.
Submission Document in Indian Patent Application No. 201747042429, dated Dec. 28, 2022, 14 pages.
Submission Document in Indian Patent Application No. 201747042429, dated Mar. 12, 2020, 9 pages.
Submission Document in Indian Patent Application No. 201947022655, dated Apr. 16, 2021, 9 pages.
Submission Document in Indian Patent Application No. 201947022655, dated Aug. 17, 2022, 45 pages.
Submission Document in Indian Patent Application No. 201947022655, dated Dec. 10, 2021, 5 pages.
Submission Document in Indian Patent Application No. 202148057534, dated Dec. 10, 2021, 129 pages.
Submission Document in Indian Patent Application No. 202148057534, dated Oct. 28, 2022, 5 pages.
Submission Document in Indonesian Patent Application No. P00201603922, dated May 17, 2019, 5 pages (with English Translation).
Submission Document in Israeli Patent Application No. 255901, dated Jan. 21, 2019, 8 pages (with English Translation).

(56) References Cited

OTHER PUBLICATIONS

Submission Document in Israeli Patent Application No. 267159, dated May 28, 2020, 4 pages (with English Translation).
Submission Document in Japanese Patent Application No. P2018-567437, dated Jul. 30, 2019, 15 pages (with English Translation).
Submission Document in Japanese Patent Application No. P2023-546948, dated Dec. 26, 2023, 4 pages (with English Translation).
Submission Document in Jordan Patent Application No. 3732014, dated Jan. 28, 2020, 2 pages (with English Translation).
Submission Document in Korean Patent Application No. 10-2016-7015608, dated Feb. 19, 2020, 9 pages (with English Translation).
Submission Document in Korean Patent Application No. 10-2016-7015608, Mar. 8, 2021, 12 pages (with English Translation).
Submission Document in Korean Patent Application No. 10-2017-7033876, dated Mar. 22, 2023, 22 pages (with English Translation).
Submission Document in Korean Patent Application No. 10-2019-7016853, dated Mar. 7, 2023, 25 pages (with English Translation).
Submission Document in Malaysian Patent Application No. PI2016702025, dated Oct. 4, 2018, 2 pages.
Submission Document in Mexican Patent Application No. MX/a/2017/015257, dated Mar. 10, 2021, 12 pages (with English Translation).
Submission Document in Mexican Patent Application No. MX/a/2017/015257, dated Nov. 26, 2020, 14 pages (with English Translation).
Submission Document in Mexican Patent Application No. MX/a/2019/006504, dated Oct. 23, 2020, 14 pages (with English Translation).
Submission Document in New Zealand Patent Application No. 720718, dated Sep. 28, 2020, 5 pages.
Submission Document in Pakistani Patent Application No. 907/2014, dated Nov. 23, 2016, 6 pages (English Translation).
Submission Document in Peruvian Patent Application No. 000711-2016, dated Dec. 23, 2019, 8 pages (with English Translation).
Submission Document in Russian Patent Application No. 2016122867, dated Aug. 31, 2018, 8 pages.
Submission Document in Russian Patent Application No. 2017141763, dated Mar. 23, 2020, 12 pages (with English Translation).
Submission Document in Russian Patent Application No. 2017141763, dated Nov. 12, 2019, 15 pages (with English Translation).
Submission Document in Russian Patent Application No. 2019120680, dated Mar. 17, 2021, 10 pages (with English Translation).
Submission Document in Singaporean Patent Application No. 11201709593V, dated Feb. 19, 2021, 18 pages.
Submission Document in Singaporean Patent Application No. 11201904020S, dated Jan. 31, 2020, 14 pages.
Submission Document in Singaporean Patent Application No. 11201904020S, dated Jul. 1, 2021, 13 pages.
Submission Document in Taiwanese Patent Application No. 103144928, dated Sep. 5, 2018, 32 pages (English Translation).
Submission Document in U.S. Appl. No. 16/465,277, dated Apr. 11, 2022, 16 pages.
Submission Document in U.S. Appl. No. 16/465,277, dated Dec. 10, 2021, 20 pages.
Submission Document in U.S. Appl. No. 16/465,277, dated Dec. 6, 2023, 2 pages.
Submission Document in U.S. Appl. No. 16/465,277, dated Feb. 17, 2023, 18 pages.
Submission Document in U.S. Appl. No. 16/465,277, dated Jan. 19, 2024, 7 pages.
Submission Document in U.S. Appl. No. 16/465,277, dated Jun. 11, 2020, 16 pages.
Submission Document in U.S. Appl. No. 16/465,277, dated Jun. 26, 2024, 10 pages.
Submission Document in U.S. Appl. No. 16/465,277, dated Jun. 8, 2023, 14 pages.
Submission Document in U.S. Appl. No. 16/465,277, dated Mar. 8, 2024, 5 pages.
Submission Document in U.S. Appl. No. 16/465,277, dated Oct. 19, 2023, 14 pages.
Submission Document in U.S. Appl. No. 16/465,277, dated Oct. 28, 2022, 14 pages.
Submission Document in U.S. Appl. No. 16/465,277, dated Sep. 13, 2024, 23 pages.
Submission Document in Venezuelan Patent Application No. 2014001560, dated Mar. 9, 2020, 4 pages (with English Translation).
Submission Document in Vietnamese Patent Application No. 1-2016-02104, dated Jun. 5, 2018, 18 pages (English Translation).
Turcios et al., "Sorafenib and FH535 in combination act synergistically on hepatocellular carcinoma by targeting cell bioenergetics and mitochondrial function," Digestive and Liver Disease, Jun. 2017, 49(6):697-704.
Van Amerongen et al., "Break the loop, escape the cycle?," The EMBO Journal, Jul. 17, 2013, 32(14):1967-1969.
Waaler et al., "Novel Synthetic Antagonists of Canonical Wnt Signaling Inhibit Colorectal Cancer Cell Growth," Cancer Res., 2011, 71:197-205.
Yao et al., "AV-65, a novel Wnt/β-catenin signal inhibitor, successfully suppresses progression of multiple myeloma in a mouse model," Blood Cancer J, 2011, 1:e43, 9 pages.
Zhao et al., "Basics for the design and development of new drugs," Shandong University Press, 2015, pp. 93-94 (with English Translation).
Chen et al., "Wnt/β-Catenin Pathway Activation Mediates Adaptive Resistance to BRAF Inhibition in Colorectal Cancer," Mol. Cancer Ther., Apr. 2018, 17(4):806-813.
International Preliminary Report on Patentability in International Application No. PCT/JP2023/036011, mailed on Oct. 16, 2025, 5 pages.
International Search Report in International Patent Application No. PCT/JP2023/036011, mailed on Nov. 7, 2023, 3 pages (English Translation).
Ishii, "Progress of research and development of MAPK pathway inhibitors," Folia Pharmacol. Jpn., 2013, 141, pp. 15-21, 18 pages. (with Machine Translation).
Kamerkar et al., "Exosomes facilitate therapeutic targeting of oncogenic KRAS in pancreatic cancer," Nature, Jun. 2017, 546:498-503.
Kim et al., "A hidden oncogenic positive feedback loop caused by crosstalk between Wnt and ERK Pathways," Oncogene, Jul. 2007, 26(31):4571-4579.
Korakis et al., "EXPAND-1, a phase I/II study with ANV600, a novel PD-1 targeted IL-2R-βγ agonist, in monotherapy and in combination with pembrolizumab, in patients with advanced solid tumors," Poster TPS2701, ASCO 2025 Annual Meeting, May 30-Jun. 3, 2025, Chicago, IL; Journal of Clinical Oncology, May 28, 2024, 43(16_suppl), 1 page.
Li et al., "A phase I/II study of first-in-human trial of JAB-21822 (KRAS G12C inhibitor) in advanced solid tumors," Poster 3089, ASCO 2022 Annual Meeting, Jun. 3-7, 2022, Chicago, IL; Journal of Clinical Oncology, Jun. 2, 2022, 40(16_suppl), 1 page.
Madhyastha et al., "Validated HPLC-MS/MS method for quantitation of AMG 510, a KRAS G12C inhibitor, in mouse plasma and its application to a pharmacokinetic study in mice," Biomedical Chromatography, Jan. 19, 2021, 35(4):1-8.
Office Action in Taiwanese Patent Application No. 111133779, dated Sep. 26, 2025, 8 pages.
Sakai, "Anti-cancer drugs for which research started and was approved in Japan: From development history to current status. Trametinib," Journal of Clinical and Experimental Medicine, Aug. 29, 2015, 254(9):796-800, 11 pages (with Machine Translation).
Taveras et al., "Ras Oncoprotein Inhibitors: The Discovery of Potent, Ras Nucleotide Exchange Inhibitors and the Structural Determination of a Drug-Protein Complex," Bioorganic & Medicinal Chemistry, Jan. 1997, 5(1):125-133.
Yamada et al., "E7386, a Selective Inhibitor of the Interaction between β-Catenin and CBP, Exerts Antitumor Activity in Tumor Models with Activated Canonical Wnt Signaling," Cancer Res., Feb. 2021, 81 (4):1052-1062.
Zhan et al., "MEK inhibitors activate Wnt signalling and induce stem cell plasticity in colorectal cancer," Nat. Commun., May 2019, 10:2197, 17 pages.

(56) References Cited

OTHER PUBLICATIONS

Zhang et al., "Chemical acylation of an acquired serine suppresses oncogenic signaling of K-Ras(G12S)," Nat. Chem. Biol., Nov. 2022, 18(11):1177-1183.
Submission Document in Brazilian Patent Application No. BR112024018041-7, dated Jan. 16, 2026, 21 pages (with English translation).
Submission Document in Chinese Patent Application No. 202380095082.X, dated Dec. 23, 2025, 28 pages (with English translation).
Submission Document in Russian Patent Application No. 2024126102, dated Jan. 19, 2026, 19 pages (with English translation).
Notice of Allowance in Japanese Patent Application No. P2023-546948, dated Feb. 20, 2024, 6 pages (with English Translation).
Chen et al., "Emerging strategies to target RAS signaling in human cancer therapy," Journal of Hematology & Oncology, 2021, 14(1):116, 23 pages.
Extended European Search Report in European Patent Application No. 23780756.5, dated Dec. 22, 2025, 10 pages.
Kanda et al., "NF-κB suppression synergizes with E7386, an inhibitor of CBP/β-catenin interaction, to block proliferation of patient-derived colon cancer spheroids," Biochemical and Biophysical Research Communication, Jan. 2022, 586:93-99.
Mashkovsky, "Medicinal Products (Lekarstvennye sredstva): Manual for Physicians," Moscow, Novaya Volna, Publisher S. B. Divov., 2001, 1:11, 6 pages (with English translation).
Office Action in Russian Patent Application No. 2024102374, dated Mar. 3, 2026, 17 pages (with English translation).
Office Action in Chinese Patent Application No. 202280052902.2, dated Jun. 3, 2026, 13 pages (with English translation).
Pathak et al., "A Phase 1 Oral Mass Balance and Combined Intravenous [$^{14}C$] Microtracer Study to Characterize the Absorption, Metabolism, Excretion, and Pharmacokinetics of Antitumor Drug E7386 in Humans," The Journal of Clinical Pharmacology, May 14, 2026, 66(5):e70202, 12 pages.

* cited by examiner

PHARMACEUTICAL COMPOSITION FOR TREATING SOLID TUMORS

TECHNICAL FIELD

The present invention relates to a pharmaceutical composition for treating a solid tumor.

BACKGROUND ART

The Wnt/β-catenin signaling pathway is a signaling pathway that is highly conserved throughout animal evolution processes, and regulates gene expression involved in cell proliferation and differentiation, body axis and organ formation, and the like. Abnormal activation of the Wnt/β-catenin signaling pathway is known to occur in various cancers including colorectal cancer and hepatocellular carcinoma.

When the Wnt ligand binds to a receptor such as Frizzled receptor on the cell membrane surface, the activity of GSK-3β (glycogensynthase kinase) is suppressed through the intracellular molecule Dvl, resulting in release of β-catenin (Catenin-beta-1) from a complex consisting of GSK-3β, AXIN, APC and β-catenin. The released and stabilized β-catenin migrates into the cell nucleus and forms a complex with the transcription factor TCF/LEF (T-cell factor/lymphoid enhancer factor). This complex requires CREP-binding protein (CBP) or P300 protein as a transcriptional coactivator. The activated TCF/LEF induces the expression of various genes including genes of MYC, cyclin D, the TCF/LEF itself and the like. The TCF/LEF is known to be responsible for regulating the gene expression by the Wnt/β-catenin signaling pathway, as a major downstream factor of the pathway (for example, see Patent Literatures 1 and 2).

(6S,9aS)—N-benzyl-8-((6-(3-(4-ethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide represented by the formula (X) (Patent Literature 1) and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide represented by the formula (X) (Patent Literature 2) are known as compounds having a Wnt pathway modulating activity.

[Chemical Formula 1]

(X)

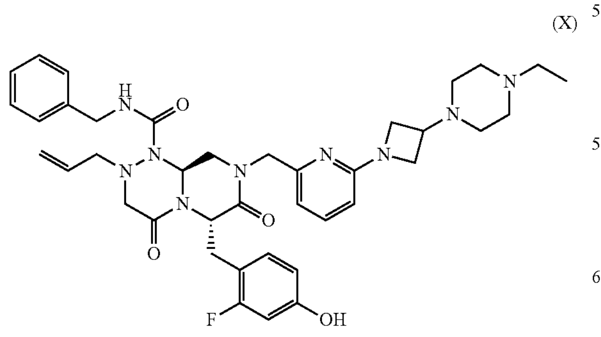

Both of the (6S,9aS)—N-benzyl-8-((6-(3-(4-ethylpiperazin-1-yl)azetidin-1-yl)pyridin-2-yl)methyl)-6-((2-fluoro-4-hydroxyphenyl)methyl)-4,7-dioxo-2-(prop-2-en-1-yl)-octahydro-1H-pyrazino[2,1-c][1,2,4]triazine-1-carboxamide disclosed in Patent Literature 1 and the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide disclosed in Patent Literature 2 are represented the formula (I) in the IUPAC nomenclature.

[Chemical Formula 2]

(I)

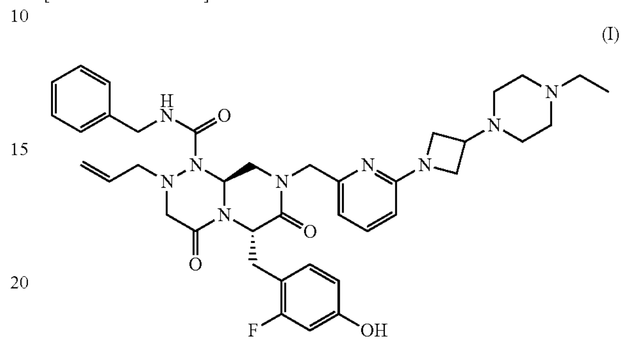

The structural formulas of the formula (X) and the formula (I) represent the same steric structure although the chemical bonds are expressed in different ways. Therefore, in the present specification, the formula (I) is used as the structural formula, and (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide is used as the chemical name.

CITATION LIST

Patent Literature

Patent Literature 1: WO 2015/098853
Patent Literature 2: WO 2016/208576

SUMMARY OF INVENTION

Technical Problem

However, there is no data on the administration, to a human subject, of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide (hereinafter, also referred to Compound A or E7386) or a pharmaceutically acceptable salt thereof, and the optimal dose and administration method thereof are still unknown. The adverse events that occur in a human subject by the administration of Compound A or the pharmaceutically acceptable salt thereof, and a method for repressing the adverse events are also unknown.

Accordingly, an object of the present invention is to provide a pharmaceutical composition or formulation containing Compound A or a pharmaceutically acceptable salt thereof, for administration to a human subject in suitable dosage and administration. The present invention also provides a method for suppressing a gastrointestinal symptom associated with administration of Compound A.

In general, there are individual differences in reaction after administration of an anticancer agent, and further individualized management is required for pain that occurs as a side effect. Chemotherapy-induced nausea and vomiting (CINV) are typical side effects which are painful for patients, and their adequate control is thereby important. Although guidelines on CINV have been established in Europe, the United States and Japan, and CINV has been improved, control of CINV is still difficult because individual differences and patient background factors are required to be considered. In addition, the method for managing CINV differs depending on the onset time, and thereby requires the patient's cooperation such as reporting detailed information including the onset time and onset frequency. There is a need for suppressing the nausea and vomiting associated with anticancer treatment with less burden and with greater precision in the field of anticancer treatment using an anticancer agent.

Solution to Problem

The present invention provides the following [1] to and [P1] to [P14].

[1]

A pharmaceutical composition for treating a solid tumor, comprising (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide represented by the formula (I) or a pharmaceutically acceptable salt thereof, wherein:

the pharmaceutical composition is administered to a human subject in combination with an effective amount of a 5-$HT_3$ receptor antagonist to suppress gastrointestinal symptom in such a manner that the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof is administered twice daily at a dose of about 10 mg to about 150 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide; and the gastrointestinal symptom is a gastrointestinal symptom associated with administration, to the human subject, of the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof.

[Chemical Formula 3]

(I)

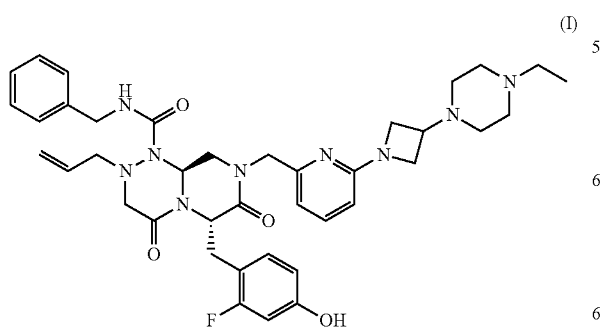

[2]

The pharmaceutical composition according to [1], wherein the gastrointestinal symptom is at least one selected from nausea and vomiting.

[3]

The pharmaceutical composition according to [1] or [2], which is administered in such a manner that the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof is administered at a dose of about 120 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[4]

The pharmaceutical composition according to any one of [1] to [3], which is administered in combination with the 5-$HT_3$ receptor antagonist simultaneously or separately.

[5]

The pharmaceutical composition according to any one of [1] to [4], wherein the 5-$HT_3$ receptor antagonist is at least one selected from the group consisting of azasetron, ondansetron, indisetron, ramosetron, granisetron and palonosetron, and a pharmaceutically acceptable salt thereof.

[6]

The pharmaceutical composition according to any one of [1] to [5], which is administered in combination with a dosage of about 0.1 mg to about 100 mg of the 5-$HT_3$ receptor antagonist as a daily dose.

[7]

The pharmaceutical composition according to any one of [1] to [6], wherein the 5-$HT_3$ receptor antagonist is at least one selected from ramosetron hydrochloride and granisetron hydrochloride.

[8]

The pharmaceutical composition according to any one of [1] to [6], wherein the 5-$HT_3$ receptor antagonist is ondansetron hydrochloride hydrate.

[9]

The pharmaceutical composition according to any one of [1] to [6], wherein the 5-$HT_3$ receptor antagonist is palonosetron hydrochloride.

[10]

The pharmaceutical composition according to any one of [1] to [7], wherein the 5-$HT_3$ receptor antagonist is granisetron hydrochloride and administered in combination once daily at a dose of about 2 mg of granisetron.

[11]

The pharmaceutical composition according to any one of [1] to [7], wherein the 5-$HT_3$ receptor antagonist is ramosetron hydrochloride and administered once daily at a dose of about 0.1 mg of ramosetron.

[12]

The pharmaceutical composition according to any one of [1] to [11], wherein the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof is (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

[13]

(6S,9aS)—N-Benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide represented by the formula (I) or a pharmaceutically acceptable salt thereof, for use in the treatment of a solid tumor, wherein:

the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof is administered to a human subject twice daily at a dose of about 10 mg to about 150 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide in combination with an effective amount of a 5-$HT_3$ receptor antagonist to suppress a gastrointestinal symptom; and the gastrointestinal symptom is a gastrointestinal symptom associated with administration, to the human subject, of the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof.

[Chemical Formula 4]

(I)

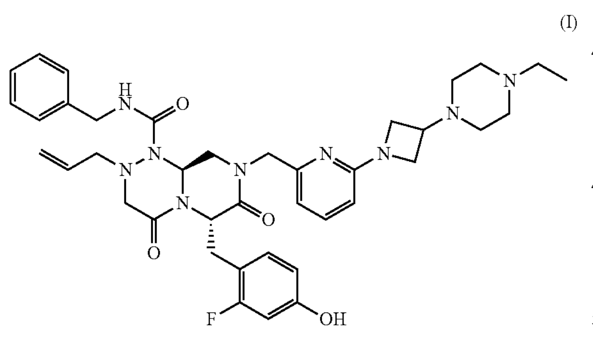

[14]

The use of (6S,9aS)—N-Benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide represented by the formula (I) or a pharmaceutically acceptable salt thereof, for manufacturing a pharmaceutical composition for treating a solid tumor, wherein:

the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof is administered to a human subject twice daily at a dose of about 10 mg to about 150 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide in combination with an effective amount of a 5-$HT_3$ receptor antagonist to suppress a gastrointestinal symptom; and the gastrointestinal symptom is a gastrointestinal symptom associated with administration, to the human subject, of the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof.

[Chemical Formula 5]

(I)

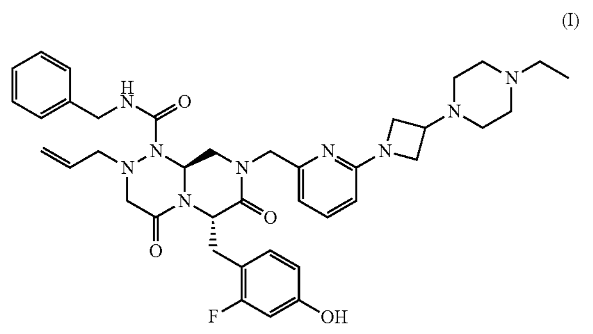

[15]

A method for treating a solid tumor, the method comprising:

administering, to a human subject with the solid tumor, (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or a pharmaceutically acceptable salt thereof twice daily at a dose of about 10 mg to about 150 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide; and administering an effective amount of a 5-$HT_3$ receptor antagonist to suppress a gastrointestinal symptom in combination to the human subject;

wherein the gastrointestinal symptom is a gastrointestinal symptom associated with administration, to the human subject, of the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof.

[Chemical Formula 6]

(I)

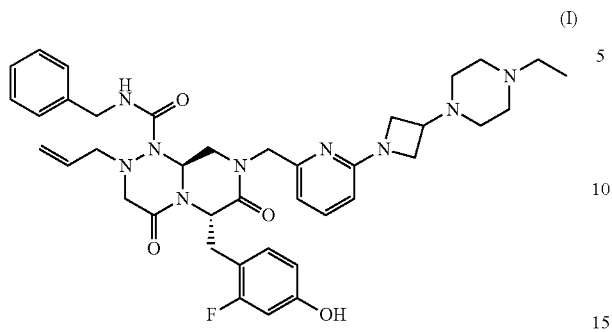

[16]

A method for administering (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or a pharmaceutically acceptable salt thereof to a human subject, the method comprising:

administering, to a human subject with the solid tumor, (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof twice daily at a dose of about 10 mg to about 150 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide; and administering an effective amount of a 5-$HT_3$ receptor antagonist to suppress a gastrointestinal symptom in combination to the human subject;

wherein the gastrointestinal symptom is a gastrointestinal symptom associated with administration, to the human subject, of the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof.

[Chemical Formula 7]

(I)

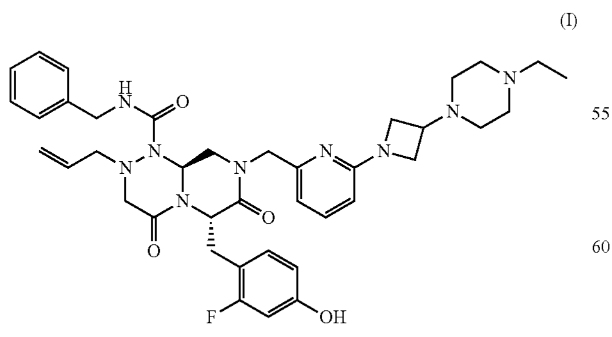

[17]

A method for treating a solid tumor while suppressing a gastrointestinal symptom, the method comprising:

administering, to a human subject with the solid tumor, (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or a pharmaceutically acceptable salt thereof twice daily at a dose of about 10 mg to about 150 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide; and administering an effective amount of a 5-$HT_3$ receptor antagonist to suppress a gastrointestinal symptom in combination to the human subject with a solid tumor;

wherein the gastrointestinal symptom is a gastrointestinal symptom associated with administration, to the human subject, of the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof.

[Chemical Formula 8]

(I)

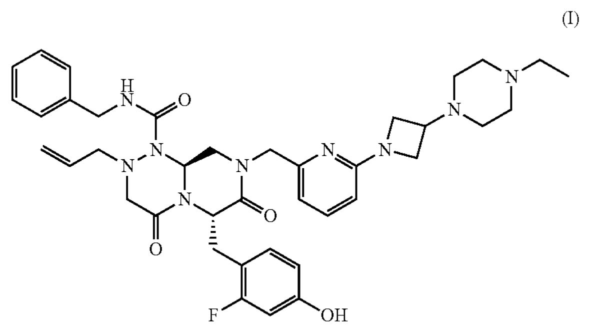 [SMILES: C=CCN1CC(=O)N2[C@@H](Cc3ccc(O)cc3F)C(=O)N(Cc3cccc(N4CC(N5CCN(CC)CC5)C4)n3)C[C@@H]2N1C(=O)NCc1ccccc1]

[18]

A method for treating a solid tumor, the method comprising:

selecting a 5-$HT_3$ receptor antagonist to suppress a gastrointestinal symptom in a human subject; and administering, to the human subject, (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or a pharmaceutically acceptable salt thereof in combination with the 5-$HT_3$ receptor antagonist in order to treat the solid tumor;

wherein:

the gastrointestinal symptom is a gastrointestinal symptom associated with administration, to the human subject, of the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof; and the gastrointestinal symptom in the human subject is suppressed.

[P1]

A medicament for use in such a manner that Compound A, which is (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide represented by the formula (I), or a pharmaceutically acceptable salt thereof is administered orally to a human subject twice daily at a dose of about 10 mg to about 150 mg per dose of Compound A.

[Chemical Formula 9]

(I)

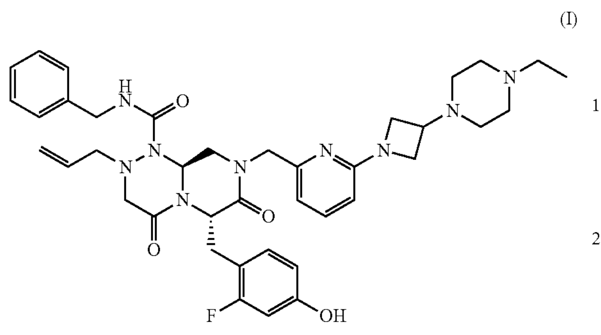

[P2]

The medicament according to [P1], which achieves an average $AUC_{(0\text{-}12\ h)}$ of about 7.58 h·ng/ml to about 31.3 h·ng/ml per 1 mg of Compound A after a single-dose administration to a human subject.

[P3]

The medicament according to [P1] or [P2], which achieves an average $AUC_{(0\text{-}12\ h)}$ of about 71.4 h·ng/ml to about 3040 h·ng/ml after a single-dose administration to a human subject.

[P4]

The medicament according to [P1] to [P3], which achieves an average Cmax of about 2.79 ng/ml to about 11.3 ng/ml per 1 mg of Compound A after a single-dose administration to a human subject.

[P5]

The medicament according to any one of [P1] to [P4], which achieves an average Cmax of about 23.5 ng/ml to about 1100 ng/ml after a single-dose administration to a human subject.

[P6]

The medicament according to any one of [P1] to [P5], wherein an $AUC_{(0\text{-}tau),ss}$ is about 7700 h·ng/ml or less after multiple-dose administration to a human subject for 8 days.

[P7]

The medicament according to any one of [P1] to [P6], which is for use in such a manner as to be administered together with a 5-$HT_3$ receptor antagonist that suppresses a gastrointestinal symptom associated with administration of the medicament according to any one of [P1] to [P6].

[P8]

The medicament according to [P7], wherein the gastrointestinal symptom is at least one selected from nausea and vomiting.

[P9]

The medicament according to [P7] or [P8], wherein the 5-$HT_3$ receptor antagonist is administered at a dose of about 0.3 mg to about 8 mg as a daily dose.

[P10]

The medicament according to any one of [P1] to [P9], which is for use in the treatment of a solid tumor.

[P11]

The medicament according to [P10], wherein the solid tumor is gastrointestinal cancer, gastrointestinal endocrine tumor, uterine cancer, malignant melanoma or lung cancer.

[P12]

The medicament according to [P9], wherein the 5-$HT_3$ receptor antagonist is selected from the group consisting of ondansetron hydrochloride hydrate, granisetron hydrochloride, palonosetron hydrochloride, dolasetron, ramosetron hydrochloride and tropisetron hydrochloride.

[P13]

A method for treating a solid tumor comprising orally administering, to a human subject, Compound A, which is (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or a pharmaceutically acceptable salt thereof twice daily at a dose of about 10 mg to about 150 mg per dose of Compound A.

[Chemical Formula 10]

(I)

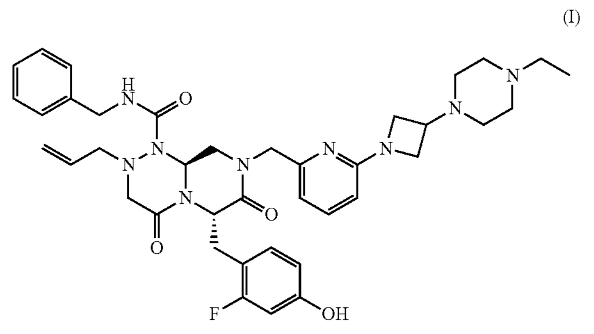 [SMILES: C=CCN1CC(=O)N2[C@@H](Cc3ccc(O)cc3F)C(=O)N(Cc3cccc(N4CC(N5CCN(CC)CC5)C4)n3)C[C@@H]2N1C(=O)NCc1ccccc1]

[P14]

The treatment method according to [P13], comprising administering a 5-$HT_3$ receptor antagonist together with Compound A or a pharmaceutically acceptable salt thereof, when the human subject develops a gastrointestinal symptom associated with administration of Compound A or a pharmaceutically acceptable salt thereof.

Advantageous Effects of Invention

According to the present invention, a medicament or formulation comprising Compound A or a pharmaceutically acceptable salt thereof for use in the dosage and administration suitable for administration to a human subject can be provided. A method for suppressing a gastrointestinal symptom associated with administration of Compound A or a pharmaceutically acceptable salt thereof can also be provided.

BRIEF DESCRIPTION OF DRAWINGS

In FIG. 3, the ordinate shows $AUC_{(0\text{-}tau),ss}$ (h*ng/ml) and the abscissa shows the values of the vomiting flag.

In FIG. 4, the ordinate shows $Cmax_{(Cmax,\ ss)}$ and the abscissa shows the values of the vomiting flag.

In FIG. 5, the ordinate shows the dosage (mg) per dose of Compound A, and the abscissa shows the value of the vomiting flag.

DESCRIPTION OF EMBODIMENTS

Figure 1:
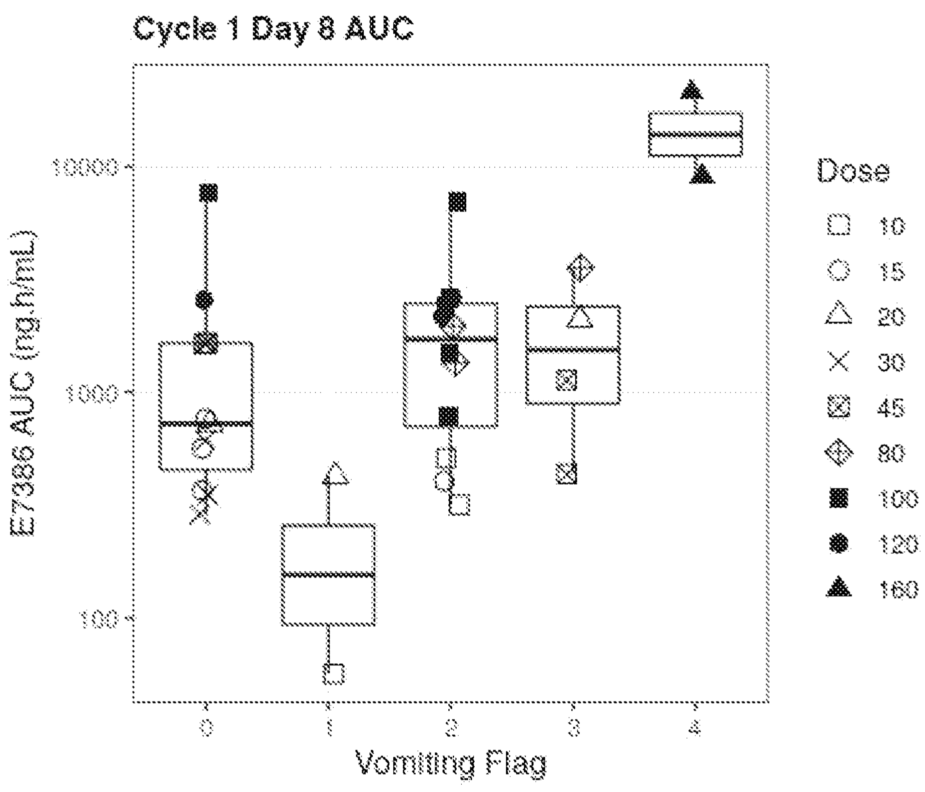
FIG. 1 is a graph showing the relationship between the in vivo pharmacokinetics of Compound A or a pharmaceutically acceptable salt thereof and the vomiting flag, and shows the $AUC_{(AUC(0\text{-}tau),ss)}$ for each test subject at the time of Cycle 1, Day 8 (C1D8).

Hereinafter, embodiments of the present invention will be described. The following embodiments are illustrative examples of the present invention, and are not intended to limit the present invention only to these embodiments. The present invention can be carried out in various modes without departing from the spirit thereof. The literatures, patent literatures such as laid-open publications, patent publications and the like cited in the present specification are incorporated herein as references.

I. Definitions

For a full understanding of the present invention described herein, the following definitions are provided for the present disclosure.

The term "human subjects" means any administration group exhibiting clinical signs or symptoms of cancer.

The expressions "bioequivalent" or "bioequivalence" are technical terms and are intended to be defined according to Approved Drug Products with Therapeutic Equivalence Evaluations, 34th edition published by the United States Department of Health and Human Services and commonly known as the "Orange Book". Bioequivalence between different formulations of the same drug substance includes equivalence with respect to rate and extent of drug absorption. For the purpose of determining whether two formulations are bioequivalent to each other, the extent and rate of absorption of the test formulation is compared to the standard formulation. Standard bioequivalence testing is carried out in a crossover manner by extensive testing including administering a single dose of a test drug and a standard drug to a number of volunteers, usually 12 to 24 healthy adults, and then measuring blood or plasma levels of the drugs over time. Detailed guidelines for establishing bioequivalence of formulations are published by the FDA, Division of Generic Drugs, Division of Bioequivalence.

Two formulations different in a PK parameter such as Cmax, AUC or tmax within −20%/+25% are generally considered to be "bioequivalent". Another approach to mean bioequivalence includes calculating a 90% confidence interval for the ratio of the means (population geometric means) of the measurements for the test and reference products. In order to establish biological compatibility, the calculated confidence interval must usually fall within the range of 80 to 125% with respect to ratio of the means for the products. In addition to this usual approach, other approaches can be useful in establishing equivalence, including (1) logarithmic transformation of pharmacokinetic data, (2) methods for evaluating order effects, and (3) methods for evaluating outlier data. For example, in (1) above, the confidence interval must usually fall within the range of 80 to 125% for the difference in the mean values of the logarithmically transformed PK parameters.

The term "formulation" refers to a mean for administering a drug substance (an active pharmaceutical ingredient (API)) or for facilitating the dosing, administration and delivery of the drug substance to a patient and other mammals. The formulations are classified in terms of the route of administration and the site of application including, for example, oral, topical, rectal, vaginal, intravenous, subcutaneous, intramuscular, intraocular, intranasal, intraaural and inhalation administration. Alternatively, the formulations are classified in terms of a physical form such as solid, semi-solid and liquid. Further, the formulations include, but not limited to a tablet, a capsule or an injection, and are subdivided based on the form, the function and the properties, as described in the Japanese Pharmacopoeia 18th edition (JP18) or the United States Pharmacopeia—NF (37) (USP37), General Edition, <1151>Papers on Pharmaceutical Preparations.

The term "excipient" means a typical inactive ingredient used as a component constituting a formulation or pharmaceutical composition.

The term "average" refers to the geometric mean. A pharmacokinetic parameter such as "average Cmax" or "average AUC" refers to the geometric mean value of Cmax or AUC.

The list of abbreviations and definitions of terms used in the present application is as follows.

AUC: area under the plasma concentration–time curve $AUC_{(0\text{-}tau)}$: area under the plasma concentration–time curve from time 0 to the time of final quantifiable concentration $AUC_{(0\text{-}inf)}$: area under the plasma concentration–time curve from 0 hours to infinite time CL/F: apparent total systemic clearance after extravascular (for example, oral) administration Cmax: maximum observed concentration t½: final elimination half-life tmax: time to maximum (peak) concentration after drug administration Cmax, ss: maximum plasma concentration in steady state tmax, ss: time to maximum plasma concentration in steady state AUC(0-tau),ss: area under the plasma concentration-time curve at each administration interval in steady state Rac(AUC): accumulation coefficient calculated from $AUC_{(0\text{-}tau),ss}$ and AUC (0-tau) after single-dose administration Rac(Cmax): accumulation coefficient calculated from $C_{max,ss}$ and $C_{max}$ after single-dose administration Effective t½ (h): effective elimination half-life Vz/F: apparent volume of distribution during terminal phase % CV: square root (exp [SD of logarithmically transformed data**2]−1)*100

The term "about" refers to a value that is 5% or less above or below the value modified by the term, unless otherwise indicated. For example, the term "about 10 mg" means a range of 9.5 mg to 10.5 mg.

Ranges can be expressed as from "about" one particular value to "about" another particular value, using the symbol "~". The specific value that is the endpoint of each range is included in that range.

As used herein, the singular forms "a", "an" and "the" includes plural referents unless the content clearly indicates otherwise.

The amount of Compound A or a pharmaceutically acceptable salt thereof contained in a medicament, pharmaceutical composition (also simply referred to as "medicament") or oral formulation according to the present disclosure is expressed in terms of the amount of Compound A in free form. For example, the term "a dose of about 10 mg per dose of Compound A" means that the dose per dose contains Compound A or the pharmaceutically acceptable salt thereof equivalent to about 10 mg of Compound A in free form. When the pharmaceutical composition or oral formulation according to the present disclosure is the form of dosage unit such as a tablet or a capsule containing a specific amount of Compound A or a pharmaceutically acceptable salt thereof, the amount of Compound A or the pharmaceutically acceptable salt thereof contained in the pharmaceutical composition or oral formulation can be determined from one or more dosage units. For example, the term "oral formulation containing about 10 mg of Compound A or a pharmaceutically acceptable salt thereof" means that the amount of Compound A or the pharmaceutically acceptable salt thereof contained in one dosage unit may be about 10 mg, or that the amount of Compound A or the pharmaceutically acceptable salt thereof contained in two or more dosage units may be about 10 mg in total.

When Compound A is in the form of a pharmaceutically acceptable salt thereof, "average Cmax for 1 mg of Compound A" or "average AUC for 1 mg of Compound A" means the average Cmax or average AUC for 1 mg of Compound A in terms of Compound A in free form.

When Compound A is in the form of a pharmaceutically acceptable salt thereof, the dosage of the pharmaceutically acceptable salt of Compound A contained in the pharmaceutical composition or oral formulation according to the present disclosure is described as value in terms of the free form of Compound A in the present application. In addition, when Compound A is in the form of a pharmaceutically acceptable salt thereof, the amount of the pharmaceutically acceptable salt of Compound A contained in the pharmaceutical composition or oral formulation is described as value in terms of the free form of Compound A in the present application.

The medicament and pharmaceutical composition according to the present disclosure comprises Compound A represented by the formula (I) or a pharmaceutically acceptable salt thereof, and can be used for the treatment of a solid tumor (also referred to as a solid cancer). The medicament and pharmaceutical composition according to the present disclosure is administered to a human subject in combination with an effective amount of a 5-$HT_3$ receptor antagonist to suppress a gastrointestinal symptom associated with the administration of Compound A or the pharmaceutically acceptable salt thereof in such a manner that Compound A or the pharmaceutically acceptable salt thereof is administered twice daily at a dose of about 10 mg to about 150 mg per dose of Compound A. The medicament and pharmaceutical composition according to the present disclosure may be administered simultaneously with or separately from the 5-$HT_3$ receptor antagonist. For example, the 5-$HT_3$ receptor antagonist may be administered before or after administration of the medicament and pharmaceutical composition according to the present disclosure. In an embodiment, the pharmaceutical composition according to the present disclosure includes both Compound A or a pharmaceutically acceptable salt thereof and the 5-$HT_3$ receptor antagonist.

The "5-$HT_3$ receptor antagonist" according to the present disclosure means any compound or biomolecule that blocks binding of serotonin (5-HT: 5-hydroxytryptamine) to a 5-$HT_3$ receptor.

"Suppressing a gastrointestinal symptom" according to the present disclosure means partially or completely alleviating, ameliorating, mitigating and/or abrogating a gastrointestinal symptom, and/or reducing the severity thereof, and/or reducing the incidence thereof.

"Gastrointestinal symptom associated with administration of Compound A", "gastrointestinal symptom associated with administration of the medicament", "gastrointestinal symptom associated with administration of the oral formulation" or "gastrointestinal symptom associated with administration of the (6S,9aS)—N-benzyl-8-({6-[3-(4-ethylpiperazin-1-yl) azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or a pharmaceutically acceptable salt thereof" according to the present disclosure means that the gastrointestinal symptom occurs after administration of the medicament, oral formulation, or Compound A or a pharmaceutically acceptable salt thereof of the present disclosure, that is, the gastrointestinal symptom is a gastrointestinal symptom that has causal relationships with Compound A. Examples of the gastrointestinal symptom include nausea, vomiting, constipation and loss of appetite and the gastrointestinal symptom may be particularly at least one selected from nausea and vomiting.

"Administered together with 5-$HT_3$ receptor antagonist" or "administered in combination with 5-$HT_3$ receptor antagonist" according to the present disclosure means that the medicament, pharmaceutical composition or oral formulation of the present disclosure and the 5-$HT_3$ receptor antagonist may be administered simultaneously or separately. It also means that the 5-$HT_3$ receptor antagonist may be administered after the human subject exhibits a gastrointestinal symptom associated with administration of the medicament, pharmaceutical composition or oral formulation of the present disclosure, or may be administered prophylactically previously or simultaneously.

As used herein, the "effective amount" of a drug, compound or 5-$HT_3$ receptor antagonist is an amount sufficient to produce any one or more beneficial or desired results.

II. Description of Embodiments

In one embodiment, the present invention provides a medicament for use in such a manner that Compound A or a pharmaceutically acceptable salt thereof is orally administered to a human subject twice daily at a dose of about 10 mg to about 150 mg per dose of Compound A.

In one embodiment, the present invention provides a pharmaceutical composition for use in such a manner that Compound A or a pharmaceutically acceptable salt thereof is orally administered to a human subject twice daily at a dose of about 10 mg to about 150 mg per dose of Compound A, wherein the pharmaceutical composition achieves an average $AUC_{(0-12\ h)}$ of about 7.58 h·ng/ml to about 31.3 h·ng/ml per 1 mg of Compound A after a single-dose administration to the human subject.

In one embodiment, the present invention provides a pharmaceutical composition for use in such a manner that Compound A or a pharmaceutically acceptable salt thereof is orally administered to a human subject twice daily at a dose of about 10 mg to about 150 mg per dose of Compound A, wherein the medicament achieves an average $AUC_{(0-12\ h)}$ of about 71.4 h·ng/ml to about 3040 h·ng/ml after a single-dose administration to the human subject.

In one embodiment, the present invention provides a pharmaceutical composition for use in such a manner that Compound A or a pharmaceutically acceptable salt thereof is orally administered to a human subject twice daily at a dose of about 10 mg to about 150 mg per dose of Compound A, wherein the pharmaceutical composition achieves an average Cmax of about 2.79 ng/ml to about 11.3 ng/ml per 1 mg of Compound A after a single-dose administration to the human subject.

In one embodiment, the present invention provides a pharmaceutical composition for use in such a manner that Compound A or a pharmaceutically acceptable salt thereof is orally administered to a human subject twice daily at a dose of about 10 mg to about 150 mg per dose of Compound A, wherein the medicament achieves an average Cmax of about 23.5 ng/ml to about 1100 ng/ml after a single-dose administration to the human subject.

In one embodiment, the present invention provides a pharmaceutical composition for use in such a manner that Compound A or a pharmaceutically acceptable salt thereof is orally administered to a human subject twice daily at a dose of about 10 mg to about 150 mg per dose of Compound A, wherein the pharmaceutical composition has an $AUC_{(0-tau),ss}$ of about 7700 h·ng/mL or less after multiple-dose administration to the human subject for 8 days.

In one embodiment, the present invention provides a medicament or pharmaceutical composition for use in such a manner that Compound A or a pharmaceutically acceptable salt thereof is orally administered to a human subject twice daily at a dose of about 10 mg to about 150 mg per dose of Compound A, wherein the medicament or pharmaceutical composition is used in such a manner as to be administered together with a $5\text{-}HT_3$ receptor antagonist that suppresses a gastrointestinal symptom associated with administration of the medicament or Compound A or the pharmaceutically acceptable salt thereof. As used herein, "administered together with $5\text{-}HT_3$ receptor antagonist" means that the medicament containing Compound A or a pharmaceutically acceptable salt thereof may be administered simultaneously with or separately from and the $5\text{-}HT_3$ receptor antagonist, and that the $5\text{-}HT_3$ receptor antagonist may be administered after a patient exhibits a gastrointestinal symptom or may be administered prophylactically previously or simultaneously.

In one embodiment, the present invention provides a pharmaceutical composition for use in such a manner that Compound A or a pharmaceutically acceptable salt thereof is orally administered to a human subject twice daily at a dose of about 10 mg to about 150 mg per dose of Compound A, wherein the medicament or pharmaceutical composition is used in such a manner as to be administered together with a $5\text{-}HT_3$ receptor antagonist that suppresses at least one selected from nausea and vomiting associated with administration of the medicament or Compound A or the pharmaceutically acceptable salt thereof.

In one embodiment, the present invention provides a pharmaceutical composition used in such a manner that Compound A or a pharmaceutically acceptable salt thereof is orally administered to a human subject twice daily at a dose of about 80 mg per dose of Compound A, wherein the pharmaceutical composition achieves an average Cmax of about 2.32 ng/ml to about 3.45 ng/ml or about 0.663 ng/ml to about 17.3 ng/ml per 1 mg of Compound A after a single-dose administration to the human subject.

In one embodiment, the present invention provides a pharmaceutical composition for use in such a manner that Compound A or a pharmaceutically acceptable salt thereof is orally administered to a human subject twice daily at a dose of about 80 mg per dose of Compound A, wherein the pharmaceutical composition achieves an average $AUC_{(0-12\ h)}$ of about 6.06 h·ng/mL to 9.48 h·ng/ml or about 2.14 h·ng/ml to about 37.2 h·ng/ml after a single-dose administration to the human subject.

In one embodiment, the present invention provides a pharmaceutical composition for use in such a manner that Compound A or a pharmaceutically acceptable salt thereof is orally administered to a human subject twice daily at a dose of about 100 mg per dose of Compound A, wherein the pharmaceutical composition achieves an average Cmax of about 3.54 ng/ml to about 5.54 ng/ml or about 2.63 ng/ml to about 11.8 ng/ml per 1 mg of Compound A after a single-dose administration to the human subject.

In one embodiment, the present invention provides a pharmaceutical composition for use in such a manner that Compound A or a pharmaceutically acceptable salt thereof is orally administered to a human subject twice daily at a dose of about 100 mg per dose of Compound A, wherein the pharmaceutical composition achieves an average $AUC_{(0-12\ h)}$ of about 11.3 h·ng/ml to about 17.8 h·ng/ml or about 3.82 h·ng/ml to about 30.4 h·ng/ml after a single-dose administration to the human subject.

In one embodiment, the present invention provides a pharmaceutical composition for use in such a manner that Compound A or a pharmaceutically acceptable salt thereof is orally administered to a human subject twice daily at a dose of about 120 mg per dose of Compound A, wherein the pharmaceutical composition achieves an average Cmax of about 3.71 ng/ml to about 5.80 ng/ml or about 2.02 ng/ml to about 11.5 ng/ml per 1 mg of Compound A after a single-dose administration to the human subject.

In one embodiment, the present invention provides a pharmaceutical composition for use in such a manner that Compound A or a pharmaceutically acceptable salt thereof is orally administered to a human subject twice daily at a dose of about 120 mg per dose of Compound A, wherein the pharmaceutical composition achieves an average $AUC_{(0-12\ h)}$ of about 12.7 h·ng/ml to 19.9 h-ng/ml or about 11.7 h·ng/ml to about 21.2 h·ng/mL after a single-dose administration to the human subject.

In yet another embodiment, the present invention provides a method for suppressing a gastrointestinal symptom associated with administration of an oral formulation containing Compound A or a pharmaceutically acceptable salt thereof and at least one pharmaceutically acceptable excipient, comprising administering a $5\text{-}HT_3$ receptor antagonist together with the oral formulation containing Compound A or the pharmaceutically acceptable salt thereof, to a patient that develops the gastrointestinal symptom associated with administration of the oral formulation containing Compound A or the pharmaceutically acceptable salt thereof and the at least one pharmaceutically acceptable excipient.

In the present specification, a pharmaceutical composition for treating a solid tumor and a method of treating a solid tumor are provided.

In the present disclosure, in an embodiment, provided is a pharmaceutical composition for treating a solid tumor, comprising Compound A represented by the formula (I) or a pharmaceutically acceptable salt thereof; wherein the pharmaceutical composition is administered to a human subject in combination with an effective amount of a 5-$HT_3$ receptor antagonist to suppress a gastrointestinal symptom in such a manner that Compound A or the pharmaceutically acceptable salt thereof is administered twice daily at a dose of about 10 mg to about 150 mg per dose of Compound A; and the gastrointestinal symptom is a gastrointestinal symptom associated with administration of Compound A or the pharmaceutically acceptable salt thereof to the human subject.

In some embodiments, the gastrointestinal symptom is at least one selected from nausea and vomiting.

In some embodiments, Compound A or a pharmaceutically acceptable salt thereof is administered at a dose of about 120 mg per dose of Compound A.

In some embodiments, the pharmaceutical composition according to the present disclosure is administered in combination with a 5-$HT_3$ receptor antagonist simultaneously or separately.

In some embodiments, the 5-$HT_3$ receptor antagonist is at least one selected from the group consisting of azasetron, ondansetron, indisetron, ramosetron, granisetron and palonosetron, or a pharmaceutically acceptable salt thereof.

In some embodiments, the pharmaceutical composition according to the present disclosure is administered in combination with a dosage of about 0.1 mg to about 16 mg of a 5-$HT_3$ receptor antagonist as daily dose.

In some embodiments, the 5-$HT_3$ receptor antagonist is at least one selected from ramosetron hydrochloride and granisetron hydrochloride.

In some embodiments, the 5-$HT_3$ receptor antagonist is granisetron hydrochloride and administered in combination once daily at a dose of about 2 mg in terms of granisetron.

In some embodiments, the 5-$HT_3$ receptor antagonist is ramosetron hydrochloride and administered once daily at a dose of about 0.1 mg in terms of ramosetron.

In some embodiments, Compound A or a pharmaceutically acceptable salt thereof is Compound A.

In the present disclosure, in an embodiment, provided is Compound A represented by the formula (I) or a pharmaceutically acceptable salt thereof, for use in the treatment of a solid tumor; wherein Compound A or the pharmaceutically acceptable salt thereof is administered to a human subject twice daily at a dose of about 10 mg to about 150 mg per dose of Compound A together with an effective amount of 5-$HT_3$ receptor antagonist to suppress a gastrointestinal symptom; and the gastrointestinal symptom is a gastrointestinal symptom associated with administration of Compound A or the pharmaceutically acceptable salt thereof to the human subject.

In the present disclosure, in an embodiment, provided is the use of Compound A represented by formula (I) or a pharmaceutically acceptable salt thereof for manufacturing a pharmaceutical composition for treating a solid tumor, wherein Compound A or the pharmaceutically acceptable salt thereof is administered to a human subject twice daily at a dose of about 10 mg to about 150 mg per dose of Compound A together with an effective amount of 5-$HT_3$ receptor antagonist to suppress a gastrointestinal symptom; and the gastrointestinal symptom is a gastrointestinal symptom associated with administration of Compound A or the pharmaceutically acceptable salt thereof to the human subject.

In the present disclosure, in an embodiment, provided is a method for treating a solid tumor, comprising: administering, to a human subject, Compound A represented by formula (I) or a pharmaceutically acceptable salt thereof twice daily at a dose of about 10 mg to about 150 mg per dose of Compound A; and administering an effective amount of a 5-$HT_3$ receptor antagonist to suppress a gastrointestinal symptom in combination to the human subject; wherein the gastrointestinal symptom is a gastrointestinal symptom associated with administration of Compound A or the pharmaceutically acceptable salt thereof to the human subject.

In the present disclosure, in an embodiment, provided is a method for administering Compound A or a pharmaceutically acceptable salt thereof to a human subject, comprising: administering, to the human subject, Compound A represented by formula (I) or the pharmaceutically acceptable salt thereof twice daily at a dose of about 10 mg to about 150 mg per dose of Compound A; and administering an effective amount of a 5-$HT_3$ receptor antagonist to suppress a gastrointestinal symptom in combination to the human subject; wherein the gastrointestinal symptom is a gastrointestinal symptom associated with administration of Compound A or the pharmaceutically acceptable salt thereof to the human subject.

In the present disclosure, in an embodiment, provided is a method for treating a solid tumor while suppressing a gastrointestinal symptom, comprising: administering, to a human subject, Compound A represented by formula (I) or a pharmaceutically acceptable salt thereof twice daily at a dose of about 10 mg to about 150 mg per dose of Compound A; and administering an effective amount of a 5-$HT_3$ receptor antagonist to suppress gastrointestinal symptoms in combination to the human subject; wherein the gastrointestinal symptom is a gastrointestinal symptom associated with administration of Compound A or a pharmaceutically acceptable salt thereof to the human subject.

In the present disclosure, in an embodiment, provided is a method for treating a solid tumor, comprising: selecting a 5-$HT_3$ receptor antagonist to suppress a gastrointestinal symptom in a human subject; and administering Compound A or a pharmaceutically acceptable salt thereof to the human subject in combination with the 5-$HT_3$ receptor antagonist in order to treat the solid tumor; wherein the gastrointestinal symptom is a gastrointestinal symptom associated with administration of Compound A or a pharmaceutically acceptable salt thereof to the human subject; and the gastrointestinal symptom in the human subject is suppressed.

In the present specification, the pharmaceutical composition is one that is administered to a human subject.

In the present specification, the oral formulation is a formulation that is administered by the oral route.

The medicament, pharmaceutical composition or oral formulation according to the present invention can be prepared by mixing at least one pharmaceutically acceptable excipient with Compound A or a pharmaceutically acceptable salt thereof. The pharmaceutical composition according to the present invention can be prepared by any known method such as the method described in Japanese Pharmacopoeia (JP) 18th edition, General Rules for Preparations or the United States Pharmacopeia—NF (37) (USP37), General Edition, <1151>Pharmaceutical Preparations.

Compound A or a pharmaceutically acceptable salt thereof is known to inhibit the β-catenin-CBP interaction, which is an important step downstream of the Wnt/β-catenin signaling pathway but not to affect the β-catenin-P300 interaction and to modulate the TCF/LEF activity that is dependent on the Wnt/β-catenin signaling pathway (for example, see WO 2015/098853 and WO 2016/208576).

The APC gene and the CTNNB1 gene are known as genes related to the Wnt signaling pathway. The APC gene is present on the long arm of chromosome 5 and is believed to be one of the causative genes of familial adenomatous polyposis (FAP). The CTNNB1 gene is a gene encoding β-catenin. In the present embodiment, it is envisaged that the pharmaceutical composition or oral formulation may be more suitable for administration to a human subject with mutations in genes involved in WNT signaling represented by abnormalities in APC and CTNNB1 genes.

In the present specification, Compound A or a pharmaceutically acceptable salt thereof can be prepared by a method known in the art such as the method described in WO 2015/098853 or WO 2016/208576.

The term "pharmaceutically acceptable salt" as used herein is not limited as long as it forms a salt with a compound represented by the formula (I) and is pharmaceutically acceptable, and examples thereof include, but are not limited to, an inorganic acid salt, an organic acid salt, an inorganic base salt, an organic base salt and an acidic or basic amino acid salt.

In the present disclosure, one embodiment of "Compound A or a pharmaceutically acceptable salt thereof" includes, for example, Compound A, that is, (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide.

The oral formulation can contain usually 0.001 to 99.5 wt %, and preferably 0.001 to 90 wt % of Compound A.

In the present embodiment, the term "carcinoma", "tumor" or "cancer" refers to the physiological condition in mammals that is typically characterized by uncontrolled cell growth.

The pharmaceutical composition or oral formulation according to the present embodiment may be effective in treating a solid tumor (also referred to as a solid cancer). The solid tumor (solid cancer) is an abnormal growth or a masse of the tissue that usually does not contain cysts or areas of fluid. Examples of the solid tumor include gastrointestinal cancer (such as esophageal cancer, gastric cancer, pancreatic cancer, biliary cancer, colorectal cancer, small intestine cancer or liver cancer), gastrointestinal endocrine tumor, uterine cancer, malignant melanoma and lung cancer. The pharmaceutical composition or oral formulation according to the present embodiment may be particularly useful for treating gastrointestinal cancer. The pharmaceutical composition or oral formulation according to the present embodiment is particularly useful for treating colorectal cancer, small intestine cancer and gastrointestinal endocrine tumor.

In the present embodiment, the "subject", "human subject" or "patient" to which the pharmaceutical composition or oral formulation is administered is a human subject in need thereof, preferably a patient that has been judged to be suffering from the above-described solid tumor (solid cancer) or to have a high possibility of suffering from it.

In the present embodiment, the medicament, pharmaceutical composition or oral formulation can contain Compound A, as a dosage per dose, in the amount of about 10 mg to about 150 mg, about 10 mg to about 120 mg, about 10 mg to about 100 mg, about 10 mg to about 80 mg, about 10 mg to about 45 mg, about 10 mg to about 30 mg, about 10 mg to about 20 mg, about 10 mg to about 15 mg, about 20 mg to about 150 mg, about 20 mg to about 120 mg, about 20 mg to about 100 mg, about 20 mg to about 80 mg, about 20 mg to about 45 mg, about 20 mg to about 30 mg, about 30 mg to about 150 mg, about 30 mg to about 120 mg, about 30 mg to about 100 mg, about 30 mg to about 80 mg, about 30 mg to about 45 mg, about 45 mg to about 150 mg, about 45 mg to about 120 mg, about 45 mg to about 100 mg, about 45 mg to about 80 mg, about 80 mg to about 150 mg, about 80 mg to about 120 mg, about 80 mg to about 100 mg, about 80 mg, about 100 mg or about 120 mg. However, the dosage per dose of the medicament, pharmaceutical composition or oral formulation is less than 160 mg in terms of Compound A. The dosage per dose is preferably about 80 mg, about 100 mg or about 120 mg in terms of Compound A, and more preferably about 100 mg or about 120 mg in terms of Compound A. In another embodiment, the dosage per dose of Compound A or a salt thereof is about 120 mg in terms of Compound A. The daily dose is about 10 mg to about 300 mg, preferably about 20 mg to about 280 mg, about 160 mg to about 240 mg or about 200 mg to about 240 mg, and more preferably about 200 mg or about 240 mg, in terms of Compound A. However, the daily dose of the pharmaceutical composition or oral formulation is less than 320 mg in terms of Compound A. The medicament, pharmaceutical composition or oral formulation is particularly preferably used in such a manner as to be administered twice daily at a dose of about 80 mg to about 120 mg per dose of Compound A. If the dosage per dose is 160 mg or more in terms of Compound A, it tends to be difficult to suppress a gastrointestinal symptom associated with (caused by) administration of Compound A or a pharmaceutically acceptable salt thereof. Therefore, the dosage per dose is less than 160 mg in terms of Compound A. Furthermore, from the results of non-clinical test, it has been believed that when the blood concentration of Compound A increases, the risk of cardiotoxicity or drug-drug interaction (DDI) may appear. Therefore, it is preferable that it is used in such a manner as to be administered twice daily from the viewpoint of the risk further reduced by lowering Cmax and of the short currently estimated half-life.

In the present specification, the term "about" means including an error of ±10% of the corresponding numerical value. For example, when "about 10 mg" is described, it includes amounts in the range of "9 mg to 11 mg".

When blood is collected after single-dose administration of the medicament, pharmaceutical composition or oral formulation according to the present embodiment to a human subject, it is preferable for the average Cmax of Compound A to reach a value within the range of about 23.5 ng/ml to about 1100 ng/ml. It is more preferable for the average Cmax of Compound A after a single-dose administration to reach a value within the range of about 29.8 ng/ml to about 870 ng/ml, about 66 ng/ml to about 1100 ng/ml, about 223 ng/ml to about 696 ng/ml or about 279 ng/mL to about 557 ng/ml.

When blood is collected after single-dose administration of the medicament, pharmaceutical composition or oral formulation according to the present embodiment to a human subject, it is preferably for the average $AUC_{(0-12\ h)}$ of Compound A to reach a value within the range of about 71.4 h·ng/ml to about 3040 h·ng/ml. It is more preferably for the average Cmax of Compound A after a single-dose administration to reach a value within the range of about 89.2 h·ng/ml to about 2430 h·ng/ml, about 105 h·ng/ml to about 2980 h·ng/ml, about 214 h·ng/ml to about 2430 h·ng/ml, about 606 h·ng/ml to about 2390 h·ng/ml or about 758 h·ng/ml to about 1920 h·ng/ml. $AUC_{(0-12\ h)}$ is the area under the curve in which the change in plasma concentration is plotted over time up to 12 hours after administration.

When blood is collected after multiple-dose administration of the medicament, pharmaceutical composition or oral formulation according to the present embodiment to a human subject for 8 days, it is preferably for the average Cmax of Compound A to reach a value within the range of about 50 ng/ml to about 2000 ng/ml. It is more preferably for the average Cmax of Compound A after sequential administration for 8 days to reach a value within the range of about 12.6 ng/ml to about 2140 ng/mL, about 318 ng/ml to about 2140 ng/ml, about 43.1 ng/mL to about 1150 ng/ml or about 589 ng/mL to about 1080 ng/mL.

When blood is collected after multiple-dose administration of the medicament, pharmaceutical composition or oral formulation according to the present embodiment to a human subject for 8 days, it is preferable for the average $AUC_{(0\text{-}tau),ss}$ of Compound A to reach a value within the range of about 45.4 h·ng/ml to about 9550 h·ng/mL. It is more preferable for the average $AUC_{(0\text{-}tau),ss}$ of Compound A after multiple-dose administration for 8 days to reach a value within the range of about 56.7 h·ng/ml to about 7640 h·ng/ml, about 56.7 h·ng/ml to about 7640 h·ng/ml, about 789 h·ng/ml to about 7640 h·ng/mL, about 1680 h·ng/mL to about 3380 h·ng/ml or about 2100 h·ng/ml to about 3400 h·ng/ml. $AUC_{(0\text{-}tau),ss}$ is the area under the plasma concentration-time curve for each administration interval at steady state.

When blood is collected after multiple-dose administration of the medicament or oral formulation according to the present embodiment to a human subject for 8 days, it is preferable for the average $AUC_{(0\text{-}tau),ss}$ of Compound A to be about 9000 h·ng/ml or less, about 8000 h·ng/mL or less, about 7700 h·ng/ml or less, or about 7640 h·ng/mL L or less. In a particular embodiment, when blood is collected after multiple-dose administration of the medicament or oral formulation according to the present embodiment to a human subject for 8 days, the average $AUC_{(0\text{-}tau),ss}$ of Compound A is about 7640 h·ng/ml or less. A gastrointestinal symptom associated with administration of the pharmaceutical composition or oral formulation according to the present embodiment can be suppressed, and the tendency for the physical and mental burden on human subjects to be reduced is increased.

In the present embodiment, it is preferable for the daily dose of the medicament or pharmaceutical composition to be such a daily dose as that it is administered orally twice daily at a dose per dose to achieve an average $AUC_{(0\text{-}12\ h)}$ of about 7.58 h·ng/ml to about 31.3 h·ng/ml per 1 mg of Compound A after a single-dose administration to a human subject. It is preferable for the daily dose of the pharmaceutical composition to be such a daily dose that it is administered orally twice daily at a dose per dose to achieve an average $AUC_{(0\text{-}12\ h)}$ of about 7.58 h·ng/mL to about 19.9 h·ng/ml per 1 mg of Compound A after a single-dose administration to a human subject.

In the present embodiment, it is preferable for the daily dose of the medicament or pharmaceutical composition to be such a daily dose that it is administered orally twice daily at a dose per dose to achieve an average Cmax of about 2.79 ng/ml to about 11.3 ng/ml per 1 mg of Compound A after a single-dose administration to a human subject. It is more preferable for the daily dose of the pharmaceutical composition to be such a daily dose that it is administered orally twice daily at a dose per dose to reach an average Cmax of about 2.79 ng/ml to about 5.54 ng/ml per 1 mg of Compound A after a single-dose administration to a human subject.

For the ranges of the average Cmax, average $AUC_{(0\text{-}12\ h)}$ and $AUC_{(0\text{-}tau),ss}$, the number of significant digits was three, and the fourth digit was rounded off. Pharmacokinetic parameters are usually approximately dose-proportional and exhibit linearity. For example, for the upper limit value, the value at 150 mg BID can be estimated from the value at 120 mg BID or 100 mg BID obtained in the Example, or by calculating the value at 1 mg in terms of Compound A. It is also possible to consider the minimum value or maximum value obtained as data for each individual at the same dose as the lower limit value or maximum value of the range, respectively, and set the range based on the values.

The medicament, pharmaceutical composition or oral formulation according to the present embodiment may be used in such a manner as to be administered together with a $5\text{-}HT_3$ receptor antagonist. Upon administration of the pharmaceutical composition or oral formulation, a patient may exhibit gastrointestinal symptoms. The gastrointestinal symptoms preferred in the present embodiment are nausea and vomiting. It is possible to suppress nausea or vomiting, which are gastrointestinal symptoms associated with administration of the pharmaceutical composition or oral formulation according to the present embodiment, by administering a $5\text{-}HT_3$ receptor antagonist, but it is difficult to suppress it by any other antiemetics.

When the patient that has received the medicament, pharmaceutical composition or oral formulation containing Compound A or a pharmaceutically acceptable salt thereof exhibits gastrointestinal symptoms, it is sufficient if the $5\text{-}HT_3$ receptor antagonist is administered. The medicament, pharmaceutical composition or oral formulation containing Compound A or a pharmaceutically acceptable salt thereof may be administered simultaneously with or separately from the $5\text{-}HT_3$ receptor antagonist. The medicament, pharmaceutical composition or oral formulation containing Compound A or a pharmaceutically acceptable salt thereof may be in the form of a kit comprising the $5\text{-}HT_3$ receptor antagonist separately. Here, "administered together with a $5\text{-}HT_3$ receptor antagonist" or "administered in combination with a $5\text{-}HT_3$ receptor antagonist" means that the medicament, pharmaceutical composition or oral formulation containing Compound A or a pharmaceutically acceptable salt thereof may be administered simultaneously with or separately from the $5\text{-}HT_3$ receptor antagonist. That is, the $5\text{-}HT_3$ receptor antagonist may be administered after the patient receiving the pharmaceutical composition or oral formulation containing Compound A or a pharmaceutically acceptable salt thereof has exhibited gastrointestinal symptoms associated with administration of the pharmaceutical composition or oral formulation according to the present embodiment, or it may be administered prophylactically before or simultaneously with administration of the pharmaceutical composition or oral formulation.

More particularly, in the present disclosure, "administered simultaneously" in "administered simultaneously or separately" means that two objects to be administered in combination are administered at the same time or at substantially the same time and by the same route of administration (simultaneous administration); and are administered separately at substantially the same time and by different routes of administration (separate administration). Here, "administered simultaneously" includes cases in which two objects are administered as one formulation. In the present disclosure, "administered separately" in "administered simultaneously or separately" means that two objects to be administered in combination are administered at the different times by the same route of administration or the different routes of administration (sequential administration). More specifically, it means the administration method in which after administration of one of two objects to be administered in combination is completed, administration of the other is started. "Administered separately" also includes cases where the frequency or duration of administration is different in the administration regimens for the two objects.

The 5-$HT_3$ receptor antagonist is a compound that exhibits an antagonistic effect on the 5-$HT_3$ receptor of which the ligand is serotonin (5-HT: 5-hydroxytryptamine). Examples of the 5-$HT_3$ receptor antagonist to be used in combination with the medicament, pharmaceutical composition or oral formulation according to the present embodiment include an antiemetic 5-$HT_3$ receptor antagonist. Examples of the 5-$HT_3$ receptor antagonistic-type antiemetic include azasetron hydrochloride, ondansetron hydrochloride hydrate, granisetron hydrochloride, palonosetron hydrochloride, dolasetron, ramosetron hydrochloride and tropisetron hydrochloride. Examples of the 5-$HT_3$ receptor antagonist to be used in combination with the pharmaceutical composition or oral formulation according to the present embodiment include azasetron, ondansetron, indisetron, ramosetron, granisetron and palonosetron, or a pharmaceutically acceptable salt thereof. In another embodiment, it is preferable for the 5-$HT_3$ receptor antagonist to be ondansetron hydrochloride hydrate, ramosetron hydrochloride, granisetron hydrochloride or palonosetron hydrochloride, and it is more preferable for the 5-$HT_3$ receptor antagonist to be ramosetron hydrochloride or granisetron hydrochloride. In some embodiments, the 5-$HT_3$ receptor antagonist is, for example, ondansetron hydrochloride hydrate. In some other embodiments, the 5-$HT_3$ receptor antagonist is, for example, ramosetron hydrochloride or granisetron hydrochloride. In some other embodiments, the 5-$HT_3$ receptor antagonist is, for example, palonosetron hydrochloride.

Ondansetron hydrochloride dihydrate (CAS registration number: 103639-04-9) is a generic name, and it is a compound having the chemical name of (±)-2,3-dihydro-9-methyl-3-[(2-methylimidazol-1-yl)methyl]carbazol-4 (1H)-one monohydrochloride dihydrate and having the following structural formula.

[Chemical Formula 11]

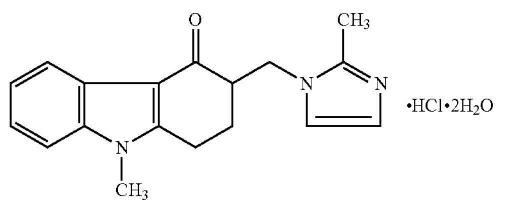

Granisetron hydrochloride (CAS registration number: 107007-99-8) is a generic name, and it is a compound having the chemical name of 1-methyl-N-(endo-9-methyl-9-azabicyclo[3.3.1]non-3-yl)-1H-indazole-3-carboxamide hydrochloride and having the following structural formula.

[Chemical Formula 12]

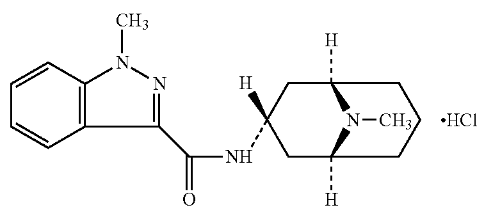

Ramosetron hydrochloride (CAS registration number: 132907-72-3) is a generic name, and it is a compound having the chemical name of (−)-(R)-5-[(1-methyl-1H-indol-3-yl)carbonyl]-4,5,6,7-tetrahydro-1H-benzimidazole monohydrochloride and having the following structural formula.

[Chemical Formula 13]

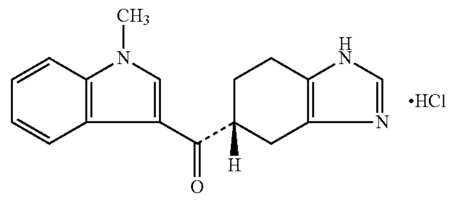

Palonosetron hydrochloride (CAS Registry Number: 135729-62-3) is a generic name, and it is a compound having the chemical name of (3aS)-2-[(3S)-quinuclidin-3-yl]-2,3,3a,4,5,6-hexahydro-1H-benzo[de]isoquinolin-1-one monohydrochloride and having the following structural formula.

[Chemical Formula 14]

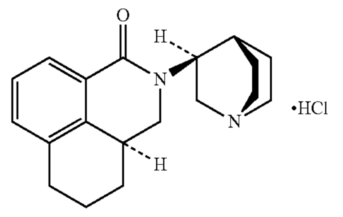

The present embodiment has an aspect of a method for treating a solid tumor (solid cancer), comprising administering, a human subject, a medicament, pharmaceutical composition or oral formulation comprising Compound A or a pharmaceutically acceptable salt and at least one pharmaceutically acceptable excipient.

Another embodiment of the present invention is a method for suppressing a gastrointestinal symptom associated with administration of Compound A or a pharmaceutically acceptable salt thereof, comprising administering a 5-$HT_3$ receptor antagonist to a patient that develops the gastrointestinal symptom associated with administration of a medicament, pharmaceutical composition or oral formulation containing Compound A or the pharmaceutically acceptable salt thereof.

Another embodiment of the present disclosure is a method for treating a tumor, comprising: administering, to a human subject with the solid tumor, Compound A or a pharmaceutically acceptable salt thereof twice daily at a dose of about 10 mg to about 150 mg per dose of Compound A; and administering an effective amount of a 5-$HT_3$ receptor antagonist to suppress a gastrointestinal symptom in combination to the human subject. The gastrointestinal symptom is associated with administration of Compound A or a pharmaceutically acceptable salt thereof to a human subject.

When a human subject exhibits a gastrointestinal symptom such as nausea or vomiting, in association with administration of a medicament, pharmaceutical composition or oral formulation containing Compound A or a pharmaceutically acceptable salt thereof, the gastrointestinal symptom can be suppressed by administering a 5-$HT_3$ receptor antagonist. Here, "suppressing" means partially or completely alleviating, ameliorating, mitigating and/or abrogating a gastrointestinal symptom, and/or reducing the severity thereof, and/or reducing the incidence thereof.

The 5-$HT_3$ receptor antagonist may be administered orally or parenterally. Examples of the dosage form of a 5-$HT_3$ receptor antagonist include a tablet, a powder, a granule, a syrup, a capsule and an internal solution. Examples of the dosage form of a 5-$HT_3$ receptor antagonist for parenteral administration include an injection, an infusion, a suspension, a cataplasm, a lotion, an aerosol and a plaster, and in one embodiment, it is an injection or an infusion. The 5-$HT_3$ receptor antagonist according to the present disclosure can be formulated, for example, by the method described in Japanese Pharmacopoeia (JP) 18th edition, the United States Pharmacopeia (USP) or European Pharmacopoeia (EP).

The dosage of a 5-$HT_3$ receptor antagonist is about 0.1 mg to about 100 mg as a daily dose. In some embodiments, the dosage of a 5-$HT_3$ receptor antagonist is about 0.1 mg to about 16 mg as a daily dose. In some embodiments, the dosage is about 0.3 mg to about 8 mg. The dosage varies depending on the age and the severity of symptoms of the subject. In the case of a commercially available prescription drug, a gastrointestinal symptom associated with administration of the pharmaceutical composition or oral formulation of the present disclosure can be more reliably suppressed by administering it according to the dosage and administration described in the package insert.

When ondansetron hydrochloride hydrate is administered as a 5-$HT_3$ receptor antagonist, for example, it is administered orally or intravenously one daily at about 4 mg in terms of ondansetron. As another embodiment, when ondansetron hydrochloride hydrate is administered, for example, it is administered orally once daily at about 24 mg or twice daily at about 8 mg, in terms of ondansetron. As other embodiments, for example, it is administered intravenously at about 8 mg, or about 0.15 mg/kg. The dosage is increased or decreased as appropriate depending on the age and symptoms of the subject. If the effect is insufficient, the same dose can be also additionally administered.

When granisetron hydrochloride is administered as a 5-$HT_3$ receptor antagonist, for example, it is administered intravenously or as an intravenous infusion once daily at 40 μg/kg in terms of granisetron. As another embodiment, when granisetron hydrochloride is administered, for example, it can be administered intravenously at 1 mg or 0.01 mg/kg in terms of granisetron. The dosage is increased or decreased as appropriate depending on the age and symptoms of the subject, but if the symptoms are not improved, it can be additionally administered once at about 40 μg/kg. When granisetron hydrochloride is administered as a 5-$HT_3$ receptor antagonist, for example, it may be administered orally once daily at a dose of 2 mg or twice daily at a dose of about 1 mg per dose of granisetron. As other embodiments, when granisetron hydrochloride is administered, for example, it is administered in the form of a patch (transdermal absorption system) of about 52 $cm^2$ containing about 34.3 mg in terms of granisetron. The dosage may be increased or decreased as appropriate depending on the age and symptoms of the subject.

When ramosetron hydrochloride is administered as a 5-$HT_3$ receptor antagonist, for example, it is administered intravenously once daily at 0.3 mg as ramosetron hydrochloride. The dosage is increased or decreased as appropriate depending on the age and symptoms of the subject. If the effect is insufficient, the same dose can be also additionally administered. However, the dose should not exceed about 0.6 mg as a daily dose. When ramosetron hydrochloride is administered as a 5-$HT_3$ receptor antagonist, for example, it may be administered orally once daily at about 0.1 mg in terms of ramosetron. The dosage may be increased or decreased as appropriate depending on the age and symptoms of the subject. The dosage may be increased or decreased as appropriate depending on the age and symptoms of the subject.

When palonosetron hydrochloride is administered as a 5-$HT_3$ receptor antagonist, for example, it may be administered once daily intravenously at about 0.75 mg or orally at about 0.5 mg in terms of palonosetron. In another embodiment, when palonosetron hydrochloride is administered, for example, it may be administered intravenously or orally at about 0.25 mg as palonosetron hydrochloride. The dosage may be increased or decreased as appropriate depending on the age and symptoms of the subject.

When dolasetron mesylate is administered as a 5-$HT_3$ receptor antagonist, for example, it is administered orally once daily at about 1.8 mg/kg or about 100 mg. The dosage may be increased or decreased as appropriate depending on the age and symptoms of the subject.

When tropisetron hydrochloride is administered as a 5-$HT_3$ receptor antagonist, for example, it may be administered orally or intravenously at a dose of about 5 mg in terms of tropisetron. The dosage may be increased or decreased as appropriate depending on the age and symptoms of the subject.

The present embodiment provides a pharmaceutical composition for treating a solid tumor, comprising Compound A or a pharmaceutically acceptable salt thereof; wherein Compound A or the pharmaceutically acceptable salt thereof is administered to a human subject in combination with an effective amount of 5-$HT_3$ receptor antagonist to suppress a gastrointestinal symptom in such a manner that Compound A or the pharmaceutically acceptable salt thereof is administered twice daily at a dose of about 10 mg to about 150 mg per dose of Compound A; and the gastrointestinal symptom is a gastrointestinal symptom associated with administration of Compound A or the pharmaceutically acceptable salt thereof to the human subject.

In a certain embodiment, provided is a pharmaceutical composition for treating a solid tumor, comprising Compound A or a pharmaceutically acceptable salt thereof; wherein Compound A or the pharmaceutically acceptable salt thereof is administered to a human subject in combination with an effective amount of 5-$HT_3$ receptor antagonist to suppress a gastrointestinal symptom in such a manner that Compound A or the pharmaceutically acceptable salt thereof is administered twice daily at a dose of about 120 mg per dose of Compound A; and the gastrointestinal symptom is at least one selected from nausea and vomiting associated with administration of Compound A or the pharmaceutically acceptable salt thereof to the human subject. Here, the "amount to suppress a gastrointestinal symptom" includes, for example, a dosage of about 0.1 mg to about 100 mg as a daily dose. The "5-$HT_3$ receptor antagonist" herein includes, for example, at least one selected from ondansetron hydrochloride hydrate, ramosetron hydrochloride and granisetron hydrochloride.

In a certain embodiment, examples of the "amount of 5-$HT_3$ receptor antagonist to suppress a gastrointestinal symptom" includes (a) ondansetron hydrochloride hydrate at a dose of about 4 mg once daily in terms of ondansetron; (b) granisetron hydrochloride at a dose of about 2 mg once daily in terms of granisetron; and (c) ramosetron hydrochloride at a dose of about 0.1 mg once daily in terms of ramosetron.

As another embodiment, provided is a pharmaceutical composition for treating a solid tumor, comprising Compound A or a pharmaceutically acceptable salt thereof; wherein Compound A or the pharmaceutically acceptable salt thereof is administered to a human subject twice daily at a dose of about 120 mg per dose of Compound A, in combination with ondansetron hydrochloride hydrate at a dose of about 4 mg once daily in terms of ondansetron; and the gastrointestinal symptom is at least one selected from nausea and vomiting associated with administration of Compound A or the pharmaceutically acceptable salt thereof to the human subject.

As another embodiment, provided is a pharmaceutical composition for treating a solid tumor, comprising Compound A or a pharmaceutically acceptable salt thereof; wherein Compound A or the pharmaceutically acceptable salt thereof is administered to a human subject twice daily at a dose of about 120 mg per dose of Compound A, in combination with granisetron hydrochloride at a dose of about 2 mg once daily in terms of granisetron; and the gastrointestinal symptom is at least one selected from nausea and vomiting associated with administration of Compound A or the pharmaceutically acceptable salt thereof to the human subject.

As another embodiment, provided is a pharmaceutical composition for treating a solid tumor, comprising Compound A or a pharmaceutically acceptable salt thereof; wherein Compound A or the pharmaceutically acceptable salt thereof is administered to a human subject twice daily at a dose of about 120 mg per dose of Compound A, in combination with ramosetron hydrochloride at a dose of about 0.1 mg once daily in terms of ramosetron; and the gastrointestinal symptom is at least one selected from nausea and vomiting associated with administration of Compound A or the pharmaceutically acceptable salt thereof to the human subject.

EXAMPLES

This study was carried out as an open-label phase I clinical trial for Compound A. The study was composed of a dose-escalation part to evaluate the safety and tolerability of Compound A, and an expansion part to evaluate the safety, tolerability and preliminary efficacy of Compound A. Each dose in the Examples is expressed as a dose of Compound A in free form.

1. Investigational Drug

Tablets containing Compound A were used as the investigational drug. Compound A was synthesized according to the method described in WO 2016/208576.

2. Subjects of Administration

Subjects of administration were test subjects that met all of the following inclusion criteria (1) to (15) and did not fall under any of the following exclusion criteria (1) to (17).

[Inclusion Criteria]

(1) Patients that have been histologically or cytologically diagnosed as solid tumor and fall under the following.
  Dose-escalation part: Patients with a solid tumor, including patients with advanced, unresectable or recurrent colorectal cancer that have no standard treatment or no other effective treatment.
  Expansion part: Patients with advanced, unresectable or recurrent colorectal cancer that have been received third-line treatment or later; or patients with a gastrointestinal cancer such as small bowel carcinoma or gastrointestinal neuroendocrine tumor that have received at least one regimen of systemic treatment by an anticancer agent after discussion and agreement with the clinical trial client (2) Dose-escalation part: It is essential for patients with colorectal cancer to receive a biopsy and submit archived tumor tissues (if archived).

Expansion part: It is essential for patients with lesions that can be biopsied to receive a biopsy. Patients with lesions that cannot be biopsied can be enrolled without any biopsy upon consultation and agreement with the clinical trial client. It is essential to submit archived tumor tissues (if archived).

(3) Survival for 12 weeks or more after administration of Compound A is expected.

(4) ECOG-PS is 0 to 1

(5)—Dose-escalation part: Japanese aged 20 years or more at the time of informed consent
  Expansion part: Patients aged 20 years or more at the time of informed consent (6) Patients in which adverse events (excluding alopecia and Grade 2 peripheral neuropathy) due to previous anti-cancer treatment have been recovered to Grades 0 to 1 (for renal/bone marrow/liver functions, until the inclusion criteria are met)

(7) Patients in which the following period has elapsed from the previous treatment before administration of Compound A a) Patients in which 3 weeks or more have elapsed after receiving chemotherapy and radiation therapy b) Patients in which 4 weeks or more have elapsed after receiving treatment with antibodies c) Patients in which 4 weeks or more have elapsed after using the investigational drug or investigational medical device d) Patients in which 2 weeks or more have elapsed after receiving treatment with blood transfusion, platelet transfusion or G-CSF formulation (8) Patients with adequate renal function (that is, serum creatinine $<2.0$ mg/dL or creatinine clearance by Cockcroft-Gault method $\geq 40$ mL/min)

(9) Patients with adequate bone marrow function (that is, neutrophil count $\geq 1{,}500/mm^3$, platelet count $\geq 100{,}000/mm^3$, and hemoglobin $\geq 9.0$ g/dL)

(10) Patients with adequate liver function (that is, international normalized ratio (INR)$\leq 1.5$ as a measure of clotting ability; total bilirubin$\leq 1.5\times$ upper limit of normal (ULN); and alkaline phosphatase (ALP), alanine aminotransferase (ALT) and aspartate aminotransferase (AST)$\leq 3\times$ULN ($\leq 5\times$ULN if liver metastasis is present)

(11) Patients with adequate levels of serum minerals (that is, calcium (albumin correction): within the normal value range, corrected calcium concentration (mg/dL) =measured calcium concentration (mg/dL)+4−serum albumin concentration (g/dL); potassium concentration of the lower limit or more of the normal value; and magnesium of the lower limit or more of the normal value)

(12) Patients that can provide written informed consent and comply with the protocol

(13) Patients with at least one measurable lesion according to RECIST 1.1

(14) Patients that agree to continuous intake of vitamin D based on the guidelines of each medical institution or the clinical judgment of the principal investigator or sub investigator, in case that 25-hydroxyvitamin D is less than 10 ng/ml

(15) Dose-escalation part: Patients that have consented to biopsy of the skin tissues other than a tumor Expansion part: At least 5 patients at each dose that consent to biopsy of the skin tissues other than a tumor

[Exclusion Criteria]

Patients that fall under any of the following criteria is excluded from the present clinical trial.

(1) Patients that fall under any of the following cardiac conditions

Patients with heart failure of class II or more according to the New York Heart Association (NYHA) functional classification Patients with unstable ischemic heart disease (myocardial infarction within 6 months before starting administration of Compound A, angina pectoris requiring nitrates twice or more weekly)

Patients with QT interval prolongation with QTcF>480 msec

Patients with left ventricular ejection fraction (LVEF) <50%

(2) Patients that have undergone major surgery within 21 days before administration of Compound A (3) Patients that are known to be unable to tolerate Compound A or excipient components (4) Patients that are known to be human immunodeficiency virus (HIV) positive (5) Patients that are known to have an active infection requiring systemic treatment (6) Patients with meningeal carcinomatosis (7) Patients that have taken the following:

Patients that have taken drugs or supplements that strongly induce cytochrome P450 (CYP) 3A or are substrates of CYP3A and have a narrow therapeutic range within 4 weeks before starting administration of Compound A Patients that have taken drugs or foods that strongly inhibit CYP3A within 2 weeks before starting administration of Compound A (8) Patients that are receiving or are scheduled to receive immunosuppressive therapy with systemic or topical steroids (more than 10 mg/day of prednisone or equivalent thereto) within 2 weeks before starting administration of Compound A (9) Patients with brain or subdural metastases. However, patients that have completed local treatment and have discontinued administration of corticosteroids 4 weeks before starting administration of Compound A are excluded. Signs (such as radiological signs) or symptoms must be stable for 4 weeks before starting administration of Compound A.

(10) Patients that have pulmonary lymphangiopathy and are in a condition of respiratory failure requiring aggressive treatment (including oxygen inhalation)

(11) Patients that are incapable of oral intake, exhibit gastrointestinal malabsorption, or exhibit other physical conditions (such as nausea, diarrhea and vomiting) judged by the principal investigator or sub investigator to be likely to affect the absorption of Compound A

(12) Patients with the following bone diseases or bone conditions:

Osteoporosis with T score less than −2.5 by DXA scan

Fasting serum β-CTX >1000 μg/mL

Osteomalacia

Hypercalcemia judged to require treatment with bisphosphonates

History of bone fracture within 6 months before starting administration of Compound A Conditions requiring orthopedic intervention Bone metastases that have not been treated with bisphosphonates or denosumab (excluding lesions treated with radiation therapy).

(13) Any conditions judged by the principal investigator or sub investigator to affect the evaluation of the study.

(14) Patients with an active malignant tumor within 24 months before starting administration of Compound A (excluding primary disease, completely treated noninvasive melanoma, basal cell carcinoma/squamous cell carcinoma of the skin, noninvasive cervical cancer/bladder cancer and early gastric cancer/colorectal cancer)

(15) Women patients that are breastfeeding or pregnant at the time of screening or baseline (Patients confirmed to be positive for human chorionic gonadotropin [hCG] or human chorionic gonadotropin β subunit [β-hCG] by urine test). However, if breastfeeding patients stop breastfeeding in order to participate in the present study, the patients are judged to be able to participate in the present study. Even if the test is negative at the time of screening, when the test has not been performed within 7 days before starting administration of Compound A, the test should be performed again.

(16) Men patients with reproductive potential and women patients with childbearing potential, the patients themselves or their partners of which do not agree to use a medically adequate contraceptive method (Note) during the study period and up to 90 days for men and up to 30 days for women after completing administration of Compound A

(17) Patients with a history of administration of Compound A

3. Method

In the dose-escalation part, the safety and tolerability of Compound A was evaluated at a plurality of doses using a 3+3 design. The starting dose of Compound A was set at 10 mg BID (twice daily).

In the expansion part, Compound A was evaluated for further safety, tolerability and preliminary efficacy. The dose considered to be tolerable from the results of the dose-escalation part or the optimal dose based on PK or PD analysis was investigated in the expansion part.

[Definition of DLT]

DLT is an adverse event that is considered to have a causal relationship with Compound A, and is the following event that occurred in Cycle 1 (for 28 days). NCI CTCAE v5.0 was used to evaluate the severity.

(a) Hematological toxicity

Grade 4 neutropenia that persists for 8 days or more even if adequate treatment including G-CSF administration has been performed Grade 3 to 4 febrile neutropenia Grade 4 thrombocytopenia Events of Grade 3 thrombocytopenia, with bleeding, persisting for 8 days or more or requiring platelet transfusion Grade 4 anemia Events of Grade 3 anemia requiring erythrocyte transfusion (b) Non-hematological toxicity
- Events of Grade 4 or more
- Grade 3 events having clinical significance (excluding diarrhea, nausea and vomiting that are recovered to Grade 0-1 within 7 days after adequate treatment)
- Grade 3 osteoporosis
- Events of Grade 2 or more bone fragility fractures, with no history of trauma or caused by a fall from a standing height or less
- In the case that the increase in fasting serum type I collagen cross-linked C-telopeptide-β isomer (B-CTX) is greater than twice from the baseline, the value is 1,000 μg/mL or more, and no amelioration to the baseline is observed within 4 weeks even after administration of bisphosphonates or denosumab
- Grade 3 to 4 laboratory test value abnormalities having clinical significance
- In the case that Compound A is interrupted for 8 days or more due to events that is judged to be intolerable by the principal investigator or sub investigator Table 1 shows the background of the subjects of administration. Most subjects (82.1%) had an Eastern Cooperative Oncology Group (ECOG) performance status of 0. Subjects with mutations in NRAS, KRAS, APC and CTNNB1 were also included. Table 1 does not include the background of the subjects to which Compound A was administered by the dosage and administration of 120 mg BID.

TABLE 1

| Characteristics | Total (N = 28) |
|---|---|
| Median age. year (range) | 59.5 (36, 77) |
| Sex, n (%) | |
| Male | 17 (60.7) |
| Female | 11 (39.3) |
| ECOG•PS, n (%) | |
| 0 | 23 (82.1) |
| 1 | 5 (17.9) |
| Median weight, kg (range) | 60.85 (42.2, 89.9) |
| Tumor type, n (%) | |
| Colorectal cancer | 16 (57.1) |
| Endometrial cancer | 2 (7.1) |
| Gastric cancer | 1 (3.6) |
| Hepatocellular carcinoma | 1 (3.6) |
| Pancreatic cancer | 2 (7.1) |
| Small bowel carcinoma | 2 (7.1) |
| Other | 4 (14.3) |
| Number of previous anti-cancer systemic medication, n (%) | |
| 0 | 3 (10.7) |
| 1 | 0 |
| 2 | 1 (3.6) |
| 3 | 2 (7.1) |
| >=4 | 22 (78.6) |
| NRAS mutation, n (%) | |
| Yes/No/Unknown | 1 (3.6)/7 (25.0)/20 (71.4) |
| KRAS mutation, n (%) | |
| Yes/No/Unknown | 7 (25.0)/5 (17.9)/16 (57.1) |
| APC mutation, n (%) | |
| Yes/No/Unknown | 10 (35.7)/1 (3.6)/17 (60.7) |
| CTNNB1 mutation, n (%) | |
| Yes/No/Unknown | 2 (7.1)/0/26 (9.3) |

The dose of Compound A was escalated or de-escalated based on the results of the first cohort of 10 mg BID according to Table 2.

TABLE 2

| Number of patients developing DLT | Management |
|---|---|
| 0 | Three subjects of administration are enrolled to the 15 mg BID cohort and the study is continued. |
| 1 | Three subjects of administration are added to the 10 mg BID cohort and the study is continued. |
| 2 or more | The dose is decreased to 5 mg BID and the study is continued. |

The dose of Compound A was further escalated or de-escalated based on the results of the additional cohort of 10 mg BID according to Table 3.

TABLE 3

| Number of patients developing DLT | Management |
|---|---|
| 0 (1 case or less out of all 6 cases) | It is judged that the dose of 10 mg BID is tolerable. Three subjects of administration are enrolled to the 15 mg BID cohort and the study is continued. |
| 1 (2 cases out of all 6 cases) | The clinical trial client, principal investigator, medical specialist and adviser on the efficacy and safety evaluation discuss whether Compound A is tolerable. |
| 2 or more (3 cases or more out of all 6 cases) | The dose is decreased to 5 mg BID and the study is continued. |

For doses more than 20 mg BID, the next dose was determined based on Table 4.

TABLE 4

| Adverse events having causal relationships with Compound A that occurred during Cycle 1 | Escalation proportion in next dose (%) |
|---|---|
| Grade 1 or less | 100% |
| Grade 2*1*2 developed in 1 case | 40-60% |
| Grade 2*1*2 developed in 2 cases or more or Grade 3*2 or more developed in 1 case or more | 25-39% |

*1 Excluding hair loss; nausea and vomiting that can be controlled with antiemetics; and laboratory test value abnormalities that do not pose a clinical problem based on the judgment of the principal investigator and sub investigator.
*2 Grade 2, Grade 3 or more adverse events that are not DLT The above was repeated to escalate the dose. It was judged that 10 mg BID was tolerable as the result of the study, and the study for 5 mg BID was therefore not performed.

4. Administration Method

[Pretreatment Phase]

In the pretreatment phase, informed consent was obtained from the subjects of administration, and a screening to confirm eligibility and a baseline evaluation to confirm the disease conditions were performed. After completing the screening, patients that met all the selection criteria and did not fall under any of the exclusion criteria were enrolled as the subjects of administration. The baseline evaluation is performed from 3 days before administration of Compound A until immediately before administration, and the disease conditions are confirmed before proceeding to the treatment phase.

[Treatment Phase]

In the treatment phase, Compound A (an oral formulation containing Compound A) is administered to the subjects of administration in one cycle of 28 days. The subjects continued to receive Compound A until disease progression, development of intolerable side effects, the desire for discontinuation of administration and consent withdrawal by the subjects of administration, or trial discontinuation by the clinical trial client. One cycle is 28 days of administration, and such an abbreviation as "C1D28" indicates the number of cycles and the number of days in the cycle, for example, "C1D28" means the 28th day of cycle 1 (the first cycle). The subjects of administration were hospitalized until the time of C1D28 and took a medical consultation and physical examination at the time of C1D15, and if the principal investigator or sub investigator was judged, from the results, that there were no medical problems, the subjects were allowed to leave the hospital. If administration was to be continued after the completion of the medical consultation and physical examination at the time of C2D1, written consent for continuation was obtained before administration at the time of C2D1.

Tablets containing Compound A are used as Compound A and administered orally repeatedly twice daily (BID). The subjects fasted 2 hours before and 1 hour after administration. The tablets were taken with water and, if possible, at the prescribed time, but if this was not possible, the tablets were taken 8 hours or more after the previous administration.

5. Evaluation (1) Pharmacokinetics

In the dose-escalation part, blood was collected from the subjects of administration according to the schedule shown in Table 5, and the pharmacokinetics of Compound A was evaluated. In the expansion part, blood was collected from the subjects of administration before the first administration at C1D1 and C1D8, 0.5, 1 and 2 hours after the oral administration of Compound A, and before the first administration at C2D1, and the pharmacokinetics of Compound A was evaluated. The data for C1D1 (the first day of the first cycle) corresponds to the results of a single-dose administration, and the data for C1D8 (the eighth day of the first cycle) corresponds to the results after multiple-dose administration for 8 days at 2 doses per 1 day.

TABLE 5

| Day of blood collection | Point of blood collection |
|---|---|
| C1D1 | Before the first administration of Compound A |
| | 0.25 Hours after the first administration of Compound A |
| | 0.5 Hours after the first administration of Compound A |
| | 1 Hours after the first administration of Compound A |
| | 2 Hours after the first administration of Compound A |
| | 4 Hours after the first administration of Compound A |
| | 6 Hours after the first administration of Compound A |
| | 8 Hours after the first administration of Compound A |
| | 12 Hours after the first administration of Compound A |
| C1D8 | Before the first administration of Compound A |
| | 0.25 Hours after the first administration of Compound A |
| | 0.5 Hours after the first administration of Compound A |
| | 1 Hours after the first administration of Compound A |
| | 2 Hours after the first administration of Compound A |
| | 4 Hours after the first administration of Compound A |
| | 6 Hours after the first administration of Compound A |
| | 8 Hours after the first administration of Compound A |
| | 12 Hours after the first administration of Compound A |
| C2D1 | Before the first administration of Compound A |
| C3D1 | Before the first administration of Compound A |
| C4D1 | Before the first administration of Compound A |
| C5D1 | Before the first administration of Compound A |
| C6D1 | Before the first administration of Compound A |

Tables 6 and 7 show the pharmacokinetic parameters at each dose in the dose-escalation part.

TABLE 6

| Dose, mg | C1D1 | | |
|---|---|---|---|
| BID (n) | $C_{max}$ (ng/mL) | $t_{max}$ (h) | $AUC_{(0-12\ h)}$ (h*ng/mL) |
| 10 mg | 37.2 | 2.00 | 131 |
| (n = 3) | (42.6) | (0.25-2.00) | (39.7) |
| 15 mg | 135 | 0.75 | 310 |
| (n = 4) | (28.9) | (0.50-2.00) | (42.5) |
| 20 mg | 146 | 1.00 | 501 |
| (n = 3) | (209) | (0.50-2.00) | (76.8) |
| 30 mg | 105 | 2.00 | 349 |
| (n = 3) | (17.7) | (2.00-2.00) | (55.5) |
| 45 mg | 209 | 1.00 | 865 |
| (n = 4) | (201) | (1.00-2.00) | (109) |
| 80 mg | 279 | 2.00 | 758 |
| (n = 3) | (251) | (1.00-2.00) | (182) |
| 100 mg | 443 | 0.50 | 1420 |
| (n = 6) | (93.9) | (0.25-4.00) | (70.5) |
| 120 mg | 557 | 2.00 | 1910 |
| (n = 3) | (72.2) | (0.50-12.0) | (7.40) |
| 160 mg | 481, 1750 | 0.50, 1.00 | 2510, 8060 |
| (n = 2) | | | |

TABLE 7

| | C1D8 | | | | | |
|---|---|---|---|---|---|---|
| Dose, mg BID(n) | $C_{max,ss}$ (ng/mL) | $t_{max,ss}$ (h) | $AUC_{(0-tau),ss}$ (h * ng/mL) | Rac (AUC) | Rac ($C_{max}$) | Effective $t_{1/2}$ (h) |
| 10 mg | 53.9 | 2.00 | 210 | 1.60 | 1.45 | 9.03-27.9[b] |
| (n = 3) | (272) | (1.00-2.00) | (168) | (113) | (178) | |
| 15 mg | 159 | 0.75 | 504 | 1.62 | 1.17 | 7.10 |
| (n = 4) | (38.1) | (0.50-2.00) | (34.3) | (52.6) | (673) | (118) |
| 20 mg | 278 | 0.50 | 866 | 1.73 | 1.90 | 12.2-18.0[b] |
| (n = 3) | (161) | (0.50-1.00) | (96.6) | (58.6) | (36.5) | |
| 30 mg | 68.3 | 2.00 | 396 | 1.13 | 0.653 | 3.27-6.81[b] |
| (n = 3) | (31.9) | (0.50-4.00) | (41.2) | (20.6) | (14.4) | |
| 45 mg | 199 | 3.00 | 1070 | 1.24 | 0.95 | 6.59 |
| (n = 4) | (124) | (1.00-400) | (69.6) | (37.0) | (63.3) | (56.3)[c] |
| 80 mg | 737 | 1.00 | 2100 | 279 | 2.64 | 17.4 |
| (n = 3) | (59.1) | (0.50-1.00) | (51.8) | (85.6) | (106) | (120) |

TABLE 7-continued

| | C1D8 | | | | | |
|---|---|---|---|---|---|---|
| Dose, mg BID(n) | $C_{max,ss}$ (ng/mL) | $t_{max,ss}$ (h) | $AUC_{(0\text{-}tau),ss}$ (h * ng/mL) | Rac (AUC) | Rac ($C_{max}$) | Effective $t_{1/2}$ (h) |
| 100 mg | 862 | 1.00 | 2700[a] | 2.18[a] | 2.13[a] | 13.0 |
| (n = 6) | (115) | (0.50-1.00) | (127) | (41.3) | (50.6) | (61.1) |
| 120 mg | 737 | 1.00 | 2460 | 1.28 | 1.32 | 5.49 |
| (n = 3) | (9.04) | (1.00-2.00) | (10.7) | (3.33) | (61.1) | (7.98) |
| 160 mg (n = 2) | 2980, 3850 | 1.00, 1.00 | 9060, 21300 | 2.64, 3.60 | 2.20, 6.20 | 17.5, 25.6 |

[a]Based on 5 patients;
[b]based on 2 patients;
[c]based on 3 patients.
$t_{max}$ is reported as median (range).
All other values are reported as geometric mean (% CV).
Parameters with two patients are reported for both patients.

Although variations were observed in the values, there was an approximate tendency that the exposure amount increased as the dosage of Compound A increased.

(2) Tolerability

The analysis of tolerability is performed using the DLT analysis subject population (the population of test subjects that have received the investigational drug as scheduled in Cycle 1 in the dose-escalation part and the population in which DLT was observed regardless of compliance with the intake of Compound A), and other analyses of safety are performed using the safety analysis subject population (the population of test subjects that have received the investigational drug once or more). This was performed using the analysis subject populations for all safety evaluations (excluding DLT evaluations).

Summary statistics for the safety data (continuous variables: number of cases, mean value, standard deviation, median, minimum and maximum values; categorical variables: number of cases and proportion) were calculated based on the actually administered treatments. In evaluation of safety, the evaluation were performed for the following: adverse events, laboratory test values, vital signs (amounts of change from the baseline in diastolic blood pressure, systolic blood pressure, pulse rate, respiratory rate and body temperature), and 12-lead electrocardiogram (percentage of test subjects with QTcF abnormality observed once or more after administration of Compound A), examination by echocardiography or MUGA scan, bone mineral density T-score by DXA scan, and ECOG-PS. The following laboratory tests were performed: hematological tests (red blood cell count, hemoglobin, hematocrit value, platelet count, white blood cell count, white blood cell fractions (neutrophils, lymphocytes, monocytes, eosinophils, basophils) coagulation test: INR), blood biochemical tests (liver function tests (AST, ALT, ALP, GGT, total bilirubin, direct bilirubin), renal function test (BUN, creatinine), other tests (blood glucose level, albumin, cholesterol, LDH, total protein, uric acid, amylase, lipase, Na, K, Cl, Ca, phosphorus, Mg, virus test: HBs antigen a, HBs antibody a, HBc antibody a, HCV antibody a, HIV antibody a, HBV DNAb, β-CTXc, 25-hydroxyvitamin Dd), and urine test (pH, protein, sugar, ketone bodies, occult blood, specific gravity)).

Tables 8 and 9 show side effects that developed after administration of Compound A, that is, treatment-emergent adverse events (TEAEs) that have causal relationships with Compound A. In the Tables, the numerical values in parentheses are the percentage of subjects in which adverse events were observed to all 28 subjects of administration listed in Table 1. It was found that high rates of nausea and vomiting were observed at all dosages of 10 mg BID to 160 mg BID. Tables 8 and 9 do not include data on the subjects to which administration was performed by the dosage and administration of 120 mg BID.

TABLE 8

| | 10 mg (N = 3) n (%) | | 15 mg (N = 4) n (%) | | 20 mg (N = 3) n (%) | | 30 mg (N = 3) n (%) | | 45 mg (N = 4) n (%) | |
|---|---|---|---|---|---|---|---|---|---|---|
| Preferred Term | Any Grade | Grade ≥3 | Any Grade | Grade ≥3 | Any Grade | Grade ≥3 | Any Grade | Grade ≥3 | Any Grade | Grade ≥3 |
| Subjects with Any Treatment-related TEAEs | 2 (66.7) | 0 | 3 (75.0) | 0 | 3 (100.0) | 1 (33.3) | 2 (66.7) | 0 | 4 (100.0) | 0 |
| Nausea | 2 (66.7) | 0 | 2 (50.0) | 0 | 2 (66.7) | 0 | 2 (66.7) | 0 | 4 (100.0) | 0 |
| Vomiting | 2 (66.7) | 0 | 1 (25.0) | 0 | 2 (66.7) | 0 | 0 | 0 | 3 (75.0) | 0 |
| Alanine aminotransferase increased | 0 | 0 | 0 | 0 | 0 | 0 | 0 | 0 | 0 | 0 |
| Anemia | 1 (33.3) | 0 | 0 | 0 | 0 | 0 | 0 | 0 | 0 | 0 |
| Aspartate aminotransferase increased | 1 (33.3) | 0 | 0 | 0 | 0 | 0 | 0 | 0 | 0 | 0 |
| Decreased appetite | 0 | 0 | 0 | 0 | 0 | 0 | 0 | 0 | 0 | 0 |
| Diarrhea | 0 | 0 | 0 | 0 | 0 | 0 | 1 (33.3) | 0 | 0 | 0 |
| White blood cell count decreased | 0 | 0 | 0 | 0 | 0 | 0 | 1 (33.3) | 0 | 0 | 0 |

TABLE 8-continued

| Preferred Term | 10 mg (N = 3) n (%) | | 15 mg (N = 4) n (%) | | 20 mg (N = 3) n (%) | | 30 mg (N = 3) n (%) | | 45 mg (N = 4) n (%) | |
|---|---|---|---|---|---|---|---|---|---|---|
| | Any Grade | Grade ≥3 | Any Grade | Grade ≥3 | Any Grade | Grade ≥3 | Any Grade | Grade ≥3 | Any Grade | Grade ≥3 |
| Amylase increased | 0 | 0 | 0 | 0 | 1 (33.3) | 0 | 0 | 0 | 0 | 0 |
| C-telopeptide increased | 0 | 0 | 0 | 0 | 0 | 0 | 0 | 0 | 1 (25.0) | 0 |
| Electrocardiogram QT prolonged | 0 | 0 | 0 | 0 | 0 | 0 | 1 (33.3) | 0 | 0 | 0 |
| Hyperphosphatemia | 0 | 0 | 0 | 0 | 1 (33.3) | 0 | 0 | 0 | 0 | 0 |
| Lipase increased | 0 | 0 | 0 | 0 | 1 (33.3) | 1 (33.3) | 0 | 0 | 0 | 0 |
| Liver disorder | 0 | 0 | 0 | 0 | 1 (33.3) | 0 | 0 | 0 | 0 | 0 |
| Osteoporosis | 0 | 0 | 0 | 0 | 0 | 0 | 0 | 0 | 0 | 0 |
| Rash | 0 | 0 | 0 | 0 | 0 | 0 | 0 | 0 | 0 | 0 |
| Sinus tachycardia | 0 | 0 | 0 | 0 | 0 | 0 | 0 | 0 | 0 | 0 |
| Stomatitis | 0 | 0 | 0 | 0 | 0 | 0 | 0 | 0 | 0 | 0 |

TABLE 9

| Preferred Term | 80 mg (N = 3) n (%) | | 100 mg (N = 6) n (%) | | 160 mg (N = 2) n (%) | | Total (N = 28) n (%) | |
|---|---|---|---|---|---|---|---|---|
| | Any Grade | Grade ≥3 | Any Grade | Grade ≥3 | Any Grade | Grade ≥3 | Any Grade | Grade ≥3 |
| Subjects with Any Treatment related TEAEs | 3 (100.0) | 0 | 6 (100.0) | 0 | 2 (100.0) | 2 (100.0) | 25 (89.3) | 3 (10.7) |
| Nausea | 3 (100.0) | 0 | 5 (83.3) | 0 | 2 (100.0) | 0 | 22 (78.6) | 0 |
| Vomiting | 3 (100.0) | 0 | 6 (100.0) | 0 | 2 (100.0) | 0 | 19 (67.9) | 0 |
| Alanine aminotransferase increased | 1 (33.3) | 0 | 2 (33.3) | 0 | 1 (50.0) | 0 | 4 (14.3) | 0 |
| Anemia | 0 | 0 | 1 (16.7) | 0 | 1 (50.0) | 1 | 3 (10.7) | 0 |
| Aspartate aminotransferase increased | 0 | 0 | 2 (33.3) | 0 | 1 (50.0) | 0 | 4 (14.3) | 0 |
| Decreased appetite | 0 | 0 | 1 (16.7) | 0 | 2 (100.0) | 2 (100.0) | 3 (10.7) | 2 (7.1) |
| Diarrhea | 0 | 0 | 0 | 0 | 1 (50.0) | 0 | 2 (7.1) | 0 |
| White blood cell count decreased | 0 | 0 | 1 (16.7) | 0 | 0 | 0 | 2 (7.1) | 0 |
| Amylase increased | 0 | 0 | 0 | 0 | 0 | 0 | 1 (3.6) | 0 |
| C-telopeptide increased | 0 | 0 | 0 | 0 | 0 | 0 | 1 (3.6) | 0 |
| Electrocardiogram QT prolonged | 0 | 0 | 0 | 0 | 0 | 0 | 1 (3.6) | 0 |
| Hyperphosphatemia | 0 | 0 | 0 | 0 | 0 | 0) | 1 (3.6) | 0 |
| Lipase increased | 0 | 0 | 0 | 0 | 0 | 0 | 1 (3.6) | 1 (3.6) |
| Liver disorder | 0 | 0 | 0 | 0 | 0 | 0 | 1 (3.6) | 0 |
| Osteoporosis | 0 | 0 | 1 (16.7) | 0 | 0 | 0 | 1 (3.6) | 0 |
| Rash | 0 | 0 | 1 (16.7) | 0 | 0 | 0 | 1 (3.6) | 0 |
| Sinus tachycardia | 0 | 0 | 1 (16.7) | 0 | 0 | 0 | 1 (3.6) | 0 |
| Stomatitis | 0 | 0 | 0 | 0 | 1 (50.0) | 0 | 1 (3.6) | 0 |

6. Suppression of Adverse Events (Nausea or Vomiting) that have Causal Relationships with Compound A In evaluation of tolerability, among the gastrointestinal symptoms associated with administration of Compound A, which were frequently observed as adverse events during Cycle 1, a method for suppressing nausea or vomiting was investigated. For subjects of administration that had the gastrointestinal symptoms, nausea or vomiting, the results of administration of various antiemetics were investigated to determine whether they could suppress the occurrence of nausea or vomiting. The antiemetics used were domperidone ($5-HT_{1A}$ receptor antagonist, Nauzelin tablet), metoclopramide (peripheral $D_2$ receptor antagonist, metoclopramide tablet), ramosetron hydrochloride ($5-HT_3$ receptor antagonist, Nasea tablet), granisetron ($5-HT_3$ receptor antagonist (Kytril tablet), and the like.

The antiemetics were timely administered to 20 subjects of administration that complained of vomiting during Cycle 1. Two subjects showed improvement by administration of prochlorperazine or metoclopramide (antiemetics other than $5-HT_3$ receptor antagonists). However, four subjects did not show improvement even after administering domperidone, metoclopramide or prochlorperazine (antiemetics other than $5-HT_3$ receptor antagonists), and afterwards, when the antiemetics were switched to ramosetron or granisetron ($5-HT_3$ receptor antagonist), they showed improvement. In twelve subjects, vomiting could be suppressed by administering ramosetron or granisetron ($5-HT_3$ receptor antagonist). Of these twelve subjects, two subjects received granisetron to prevent vomiting when they developed nausea, and vomiting could be prevented. However, in two subjects that received Compound A at a dose of 160 mg BID, vomiting could not be suppressed even by administering ramosetron or granisetron ($5-HT_3$ receptor antagonist).

The highest value of $AUC_{(0\text{-}tau),ss}$ at the time of C1D8 of the subjects in which vomiting could be suppressed vomiting by administering the $5-HT_3$ receptor antagonist was 7640 h·ng/ml. The lowest value of $AUC_{(0\text{-}tau),ss}$ at the time of C1D8 of the subjects in which vomiting could not be suppressed even after administering the $5-HT_3$ receptor antagonist was 9060 h·ng/mL.

When $AUC_{(0\text{-}tau),ss}$ at the time of C1D8 was 7640 h·ng/ml or less, it was predicted that administration of the $5-HT_3$ receptor antagonist could suppress the gastrointestinal symptom associated with administration of Compound A or a pharmaceutically acceptable salt thereof. When the $AUC_{(0\text{-}tau),ss}$ at the time of C1D8 was 9060 h·ng/ml or more, it was predicted that even if the $5-HT_3$ receptor antagonist was administered, the gastrointestinal symptom associated with administration of Compound A or a pharmaceutically acceptable salt thereof, that is, nausea or vomiting could not be suppressed. That is, it was found that at 160 mg BID, even if the $5-HT_3$ receptor antagonist was administered, it was highly possible that the gastrointestinal symptom associated with administration of Compound A or a pharmaceutically acceptable salt thereof could not be suppressed. Therefore, the recommended dose was determined to be less than 160 mg BID. It was considered that the recommended dose was about 80 mg to about 120 mg and that 100 mg BID or 120 mg BID was particularly preferred.

Figure 2:
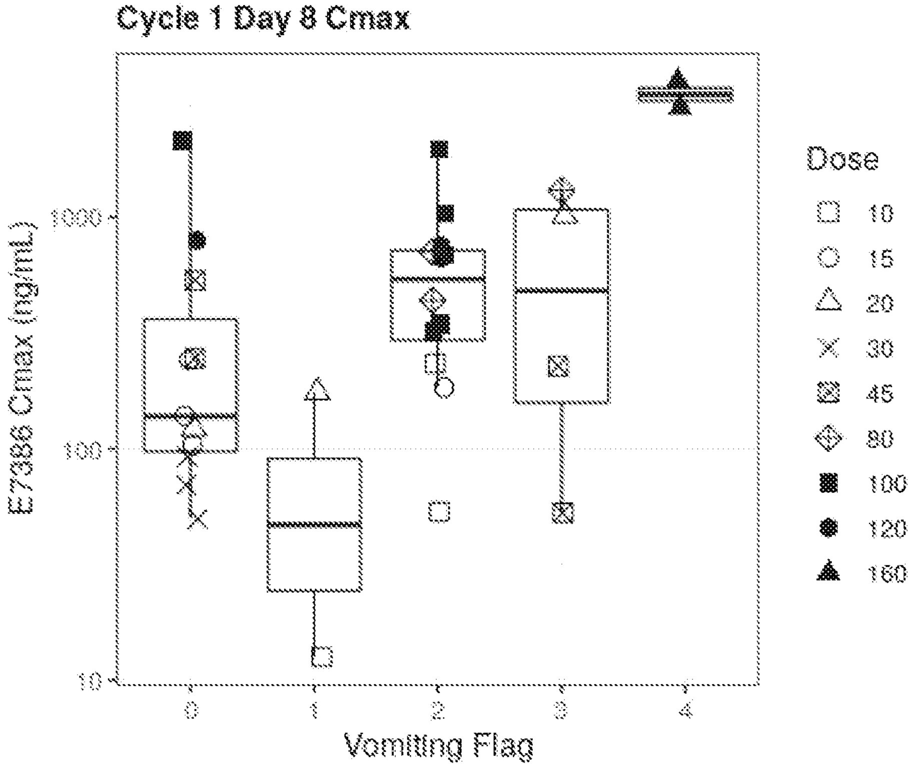
FIG. 2 is a graph showing the relationship between the in vivo pharmacokinetics of Compound A or a pharmaceutically acceptable salt thereof and the vomiting flag, and shows the relationship between $Cmax_{(Cmax,\ ss)}$ and the vomiting flag for each test subject at the time of C1D8.

FIGS. 1 and 2 are graphs showing the relationship between $Cmax_{(Cmax,ss)}$ or AUC ($AUC_{(0\text{-}tau),ss}$) and the vomiting flag for each test subject at the time of C1D8. The vomiting flags are as listed in Table 10. For example, the vomiting flag 3 means a case in which treatment with an antiemetic other than the $5-HT_3$ receptor antagonist was first attempted but vomiting could not be suppressed, and vomiting could be suppressed when the antiemetic was switched to the $5-HT_3$ receptor antagonist.

TABLE 10

| Vomiting flag | N | Condition |
|---|---|---|
| 0 | 10 | Neither nausea nor vomiting was observed, or it was not required to administer antiemetics. |
| 1 | 2 | Vomiting could be suppressed with antiemetics other than 5-HT3 receptor antagonists. |
| 2 | 12 | Vomiting could be suppressed with 5-HT3 receptor antagonists. |
| 3 | 4 | Vomiting could not be suppressed with antiemetics other than 5-HT3 receptor antagonists, but could be suppressed with 5-HT3 receptor antagonists. |
| 4 | 2 | Vomiting could not be suppressed with 5-HT3 receptor antagonists. |

7. Pharmacokinetics of Additional Cases in Dose-Escalation Part

Another five subjects of administration which received 120 mg BID were further added. Tables 11 and 12 show pharmacokinetics of 120 mg BID including the previous three patients shown in Table 7.

TABLE 11

| | C1D1 | | |
|---|---|---|---|
| Dose, mg bid, (subject #) | $C_{max}$ (ng/mL) | $t_{max}$ (h) | $AUC_{(0\text{-}12\ h)}$ (h*ng/mL) |
| 120 mg (n = 8) | 557 (72.2) | 2.00 (0.50-12.0) | 1910 (7.40) |

TABLE 12

| Dose, | C1D8 | | | | | |
|---|---|---|---|---|---|---|
| mg BID(n) | $C_{max,\ ss}$ (ng/mL) | $t_{max,\ ss}$ (h) | $AUC_{(0\text{-}tau),\ ss}$ (h*ng/mL) | Rac (AUC) | Rac ($C_{max}$) | Effective $t_{1/2}$ (h) |
| 120 mg (n = 8) | 751[a] (150) | 1.00[a] (0.50-2.00) | 2460[a] (119) | 1.31[a] (34.4) | 1.551[a] (84.7) | 751[a] (150) |

Geomean (% CV) values are shown with rounded to 3 significant figures except $t_{max}$ reported as median (range).
[a]based on n = 7 subjects Table 13 shows the occurrence status of nausea or vomiting as an adverse event having a causal relationship with Compound A in 8 cases at 120 mg BID.

TABLE 13

| | 120 mg (N = 8) n (%) | |
|---|---|---|
| Preferred Term | Any Grade | Grade ≥3 |
| Subjects with Any Treatment-related TEAEs | 8 (100.0) | 0 |
| Nausea | 7 (87.5) | 0 |
| Vomiting | 2 (25.0) | 0 |

Five additional patients were investigated whether the occurrence of nausea or vomiting, which is an adverse event having a causal relationship with Compound A, could be suppressed. Ramosetron hydrochloride or granisetron hydrochloride ($5-HT_3$ receptor antagonist) was administered to four patients of administration that complained of vomiting during Cycle 1. Of the four patients that complained of vomiting, three patients received granisetron hydrochloride to prevent the gastrointestinal symptoms (nausea, vomiting) associated with administration of Compound A.

For patients which had received granisetron hydrochloride prophylactically, no vomiting occurred afterwards, and all 5-$HT_3$ receptor antagonists could prevent nausea or vomiting among the gastrointestinal symptoms associated with administration of Compound A (vomiting flag 2). Vomiting could be also suppressed in one test subject that received granisetron hydrochloride after experiencing symptoms of nausea or vomiting (vomiting flag 2).

Figure 5:
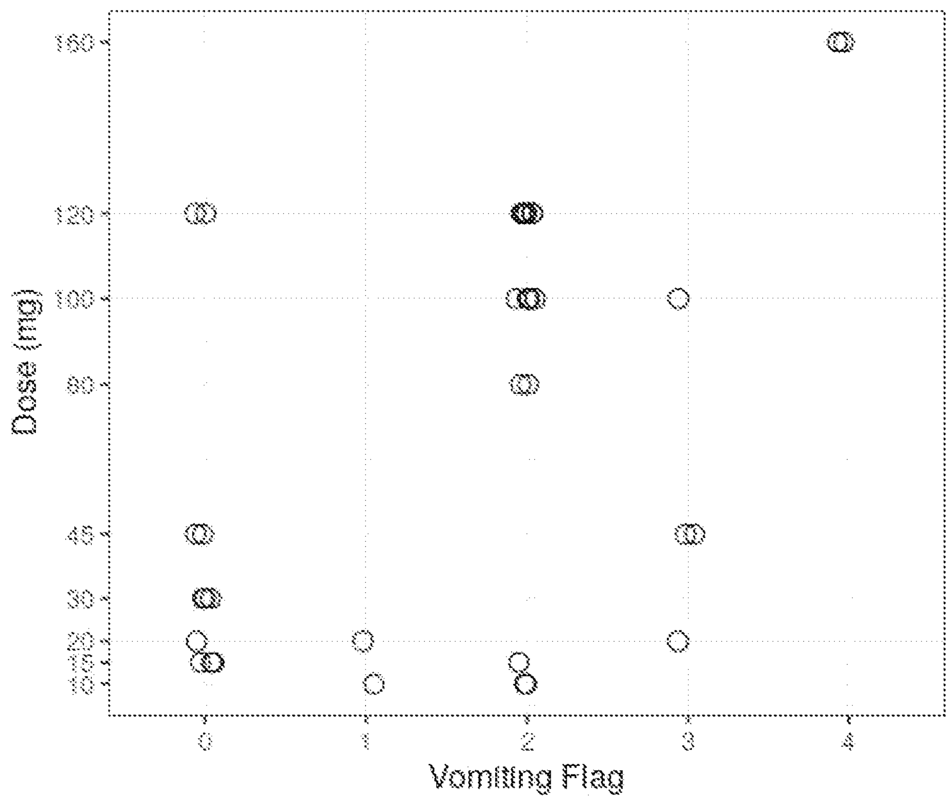
FIG. 5 is a relationship diagram for the final vomiting management in the dose-escalation part, including additional cases.

FIG. 5 and Table 14 show the results of management of emesis for the entire dose-escalation part including additional cases.

TABLE 14

| Vomiting flag | N | Condition |
|---|---|---|
| 0 | 11 | Neither nausea nor vomiting was observed, or it was not required to administer antiemetics. |
| 1 | 2 | Vomiting could be suppressed with antiemetics other than 5-HT3 receptor antagonists |
| 2 | 16 | Vomiting could be suppressed with 5-HT3 receptor antagonists. |
| 3 | 4 | Vomiting could not be suppressed with antiemetics other than 5-HT3 receptor antagonists, but could be suppressed with 5-HT3 receptor antagonists. |
| 4 | 2 | Vomiting could not be suppressed with 5-HT3 receptor antagonists. |
| Exclusion | 1 | |
| Total | 36 | |

One patient in which the vomiting flag was judged to be 3 in the previous analysis was excluded from data, because it was found, as a result of a later analysis, that vomiting or nausea were not gastrointestinal symptoms associated with the administration of Compound A.

Figure 3:
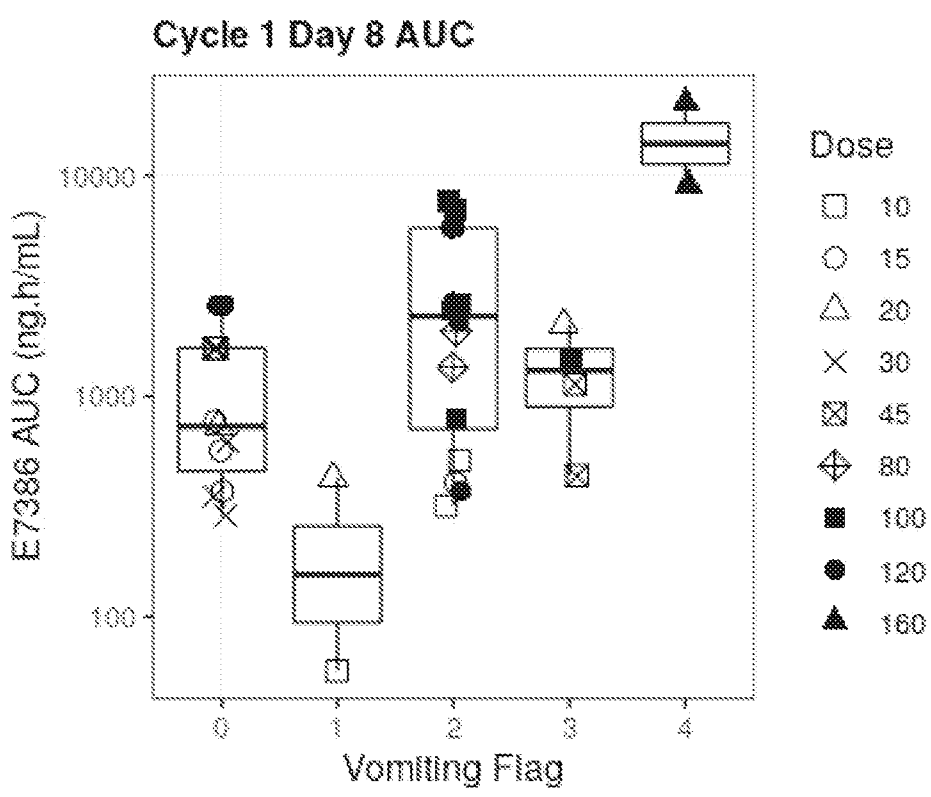
FIG. 3 is a graph showing the relationship between the in vivo pharmacokinetics of Compound A or a pharmaceutically acceptable salt thereof and the vomiting flag (the relationship for the final vomiting management in the dose-escalation part, including additional cases), and it is a diagram showing the relationship between AUC and the vomiting flag for each test subject at the time of Cycle 1, Day 8 (C1D8).
Figure 4:
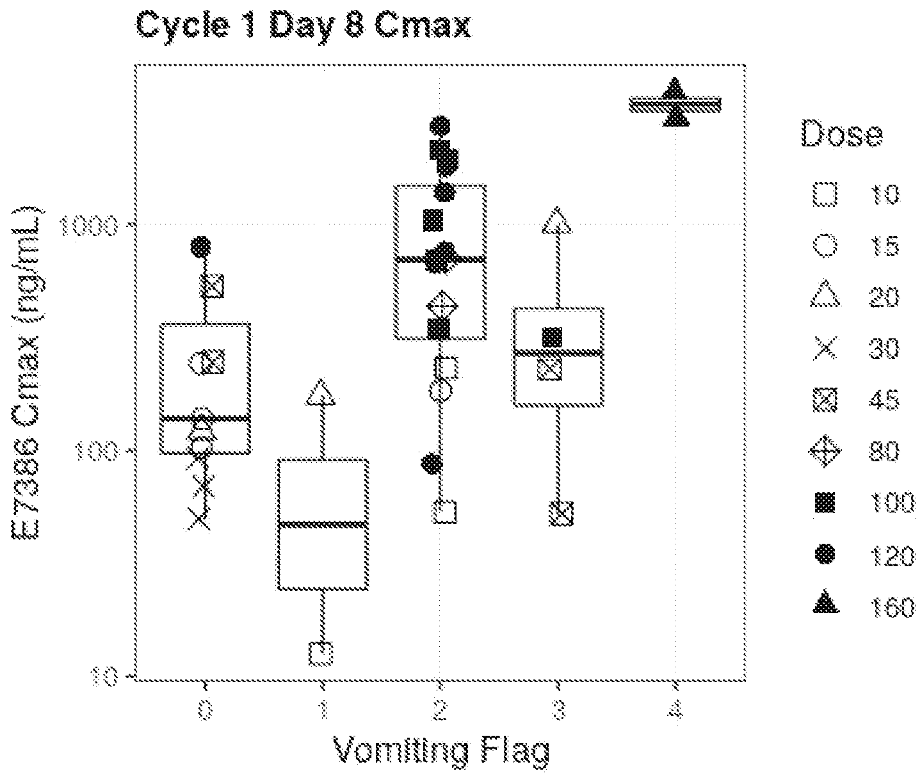
FIG. 4 is a graph showing the relationship between the in vivo pharmacokinetics of Compound A or a pharmaceutically acceptable salt thereof and the vomiting flag (the relationship for the final vomiting management in the dose-escalation part, including additional cases), and it is a diagram showing the relationship between Cmax and the vomiting flag for each test subject at the time of Cycle 1, Day 8 (C1D8).

For a total of two cases including one case at 100 mg BID and one case at 120 mg BID, data on the pharmacokinetics at the time of C1D8 could not be obtained. Therefore, one case at 100 mg BID in FIGS. 1 to 4 and one case at 120 mg BID in FIGS. 3 and 4 are plotted using the pharmacokinetic parameters at C1D1.

In addition, for the additional five cases, when $AUC_{(0\text{-}tau),ss}$ at the time of C1D8 is 7640 h·ng/ml or less, it was predicted that administration of the 5-$HT_3$ receptor antagonist could suppress the gastrointestinal symptom associated with administration of Compound A or a pharmaceutically acceptable salt thereof. Therefore, it was believed that the recommended clinical dose was about 80 mg to about 120 mg, 100 mg BID or 120 mg BID was particularly preferred, and 120 mg BID was most preferred.

The invention claimed is:

1. A method for treating a solid tumor, the method comprising:

administering, to a human subject with the solid tumor, (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide represented by the formula (I) or a pharmaceutically acceptable salt thereof twice daily at a dose of about 10 mg to about 150 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide; and administering an effective amount of a 5-$HT_3$ receptor antagonist to suppress a gastrointestinal symptom in combination to the human subject;

wherein the gastrointestinal symptom is a gastrointestinal symptom associated with administration, to the human subject, of the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino[2,1-c][1,2,4]triazine-1(6H)-carboxamide or the pharmaceutically acceptable salt thereof (I)

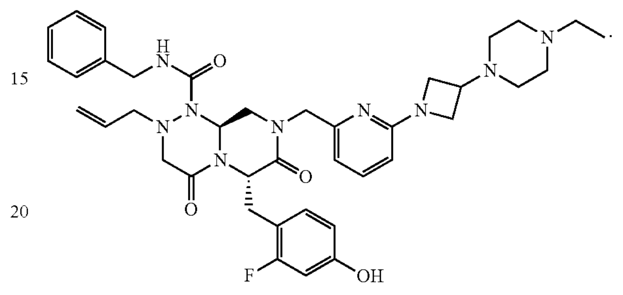

2. The method according to claim 1, wherein the gastrointestinal symptom is at least one selected from nausea and vomiting.

3. The method according to claim 1, wherein the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide or the pharmaceutically acceptable salt thereof is administered at a dose of about 120 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide.

4. The method according to claim 1, wherein the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide or the pharmaceutically acceptable salt thereof is administered in combination with the 5-$HT_3$ receptor antagonist simultaneously or separately.

5. The method according to claim 1, wherein the 5-$HT_3$ receptor antagonist is at least one selected from the group consisting of azasetron, ondansetron, indisetron, ramosetron, granisetron and palonosetron, and a pharmaceutically acceptable salt thereof.

6. The method according to claim 1, wherein the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide or the pharmaceutically acceptable salt thereof is administered in combination with a dosage of about 0.1 mg to about 100 mg of the 5-$HT_3$ receptor antagonist as a daily dose.

7. The method according to claim 1, wherein the 5-$HT_3$ receptor antagonist is at least one selected from ramosetron hydrochloride and granisetron hydrochloride.

8. The method according to claim 1, wherein the 5-$HT_3$ receptor antagonist is granisetron hydrochloride and administered in combination once daily at a dose of about 2 mg of granisetron.

9. The method according to claim 1, wherein the 5-$HT_3$ receptor antagonist is ramosetron hydrochloride and administered once daily at a dose of about 0.1 mg of ramosetron.

10. The method according to claim 1, wherein the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide or the pharmaceutically acceptable salt thereof is (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl) hexahydro-2H-pyrazino [2,1-c][1,2,4]triazine-1(6H)-carboxamide.

11. A method for treating a solid tumor while suppressing a gastrointestinal symptom, the method comprising:

administering, to a human subject with the solid tumor, (6S,9aS)—N-benzyl-8-({6-[3-(4-ethylpiperazin-1-yl) azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide represented by the formula (I) or a pharmaceutically acceptable salt thereof twice daily at a dose of about 10 mg to about 150 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide; and administering an effective amount of a 5-$HT_3$ receptor antagonist to suppress a gastrointestinal symptom in combination to the human subject with a solid tumor;

wherein the gastrointestinal symptom is a gastrointestinal symptom associated with administration, to the human subject, of the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide or the pharmaceutically acceptable salt thereof (I)

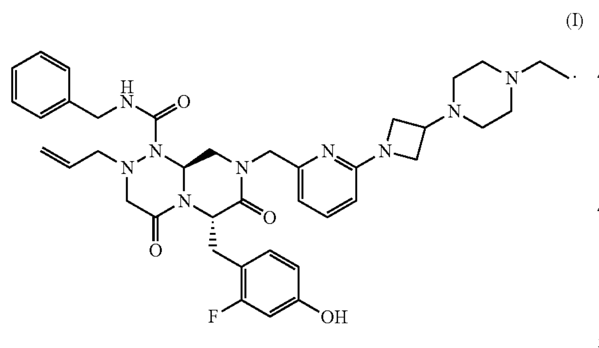

12. The method according to claim 11, wherein the gastrointestinal symptom is at least one selected from nausea and vomiting.

13. The method according to claim 11, wherein the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide or the pharmaceutically acceptable salt thereof is administered at a dose of about 120 mg per dose of (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl) hexahydro-2H-pyrazino [2,1-c][1,2,4]triazine-1(6H)-carboxamide.

14. The method according to claim 11, wherein the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide or the pharmaceutically acceptable salt thereof is administered in combination with the 5-$HT_3$ receptor antagonist simultaneously or separately.

15. The method according to claim 11, wherein the 5-$HT_3$ receptor antagonist is at least one selected from the group consisting of azasetron, ondansetron, indisetron, ramosetron, granisetron and palonosetron, and a pharmaceutically acceptable salt thereof.

16. The method according to claim 11, wherein the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide or the pharmaceutically acceptable salt thereof is administered in combination with a dosage of about 0.1 mg to about 100 mg of the 5-$HT_3$ receptor antagonist as a daily dose.

17. The method according to claim 11, wherein the 5-$HT_3$ receptor antagonist is at least one selected from ramosetron hydrochloride and granisetron hydrochloride.

18. The method according to claim 11, wherein the 5-$HT_3$ receptor antagonist is granisetron hydrochloride and administered in combination once daily at a dose of about 2 mg of granisetron.

19. The method according to claim 11, wherein the 5-$HT_3$ receptor antagonist is ramosetron hydrochloride and administered once daily at a dose of about 0.1 mg of ramosetron.

20. The method according to claim 11, wherein the (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4]triazine-1(6H)-carboxamide or the pharmaceutically acceptable salt thereof is (6S,9aS)—N-benzyl-8-({6-[3-(4-ethylpiperazin-1-yl)azetidin-1-yl]pyridin-2-yl}methyl)-6-(2-fluoro-4-hydroxybenzyl)-4,7-dioxo-2-(prop-2-en-1-yl)hexahydro-2H-pyrazino [2,1-c][1,2,4] triazine-1(6H)-carboxamide.

* * * * *